US011969348B2

(12) United States Patent
Alon

(10) Patent No.: US 11,969,348 B2
(45) Date of Patent: *Apr. 30, 2024

(54) CARDIAC VALVE REPLACEMENT

(71) Applicant: EDWARDS LIFESCIENCES CORPORATION, Irvine, CA (US)

(72) Inventor: David Alon, Zichron Yaacov (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/412,352

(22) Filed: Aug. 26, 2021

(65) Prior Publication Data

US 2021/0378825 A1  Dec. 9, 2021

Related U.S. Application Data

(60) Division of application No. 16/158,575, filed on Oct. 12, 2018, now Pat. No. 11,129,716, which is a
(Continued)

(51) Int. Cl.
*A61F 2/24* (2006.01)
*A61B 17/04* (2006.01)
(Continued)

(52) U.S. Cl.
CPC .......... *A61F 2/2466* (2013.01); *A61B 17/068* (2013.01); *A61F 2/2409* (2013.01);
(Continued)

(58) Field of Classification Search
None
See application file for complete search history.

(56) References Cited

U.S. PATENT DOCUMENTS 688,592 A  12/1901 Chadwick
3,604,488 A  9/1971 Wishart et al.
(Continued)

FOREIGN PATENT DOCUMENTS

CN  1684644 A  10/2005
CN  2782049  5/2006
(Continued)

OTHER PUBLICATIONS

Cohn, et al., "The Evolution of Mitral Valve Surgery," Am heart Hosp. J. 2003:1 pp. 40-46 (2003).
(Continued)

*Primary Examiner* — Sarah A Long
*Assistant Examiner* — Lindsey Bachman
(74) *Attorney, Agent, or Firm* — Thomas C. Richardson

(57) ABSTRACT

A heart valve annulus repair device having a tissue engaging member and a plurality of anchors. The tissue engaging member includes a loop of wire. Each of the anchors has a pointy front end and a back end and a slot that runs in a front-to-back direction. The anchors are distributed about the loop of wire with the front ends of the plurality of anchors facing the heart valve annulus and with the loop of wire passing through the slots. The device further includes means for implanting the anchors into the heart valve annulus tissue so that the tissue engaging member becomes affixed to the heart valve annulus.

19 Claims, 34 Drawing Sheets

Related U.S. Application Data continuation of application No. 14/364,060, filed as application No. PCT/IB2012/057138 on Dec. 10, 2012, now Pat. No. 10,143,553.

(60) Provisional application No. 61/683,736, filed on Aug. 16, 2012, provisional application No. 61/569,304, filed on Dec. 12, 2011.

(51) Int. Cl.

| | |
|---|---|
| *A61B 17/068* | (2006.01) |
| *A61B 17/00* | (2006.01) |
| *A61B 17/064* | (2006.01) |
| *A61B 17/115* | (2006.01) |
| *A61B 17/22* | (2006.01) |

(52) U.S. Cl.
CPC .......... *A61F 2/2418* (2013.01); *A61F 2/2445* (2013.01); *A61B 2017/00243* (2013.01); *A61B 2017/00557* (2013.01); *A61B 2017/00783* (2013.01); *A61B 2017/0403* (2013.01); *A61B 2017/0409* (2013.01); *A61B 2017/0414* (2013.01); *A61B 2017/0427* (2013.01); *A61B 2017/0438* (2013.01); *A61B 2017/0464* (2013.01); *A61B 2017/0647* (2013.01); *A61B 17/1155* (2013.01); *A61B 2017/22068* (2013.01); *A61F 2/2448* (2013.01); *F04C 2270/0421* (2013.01)

(56) References Cited

U.S. PATENT DOCUMENTS

| | | | |
|---|---|---|---|
| 3,656,185 A | 4/1972 | Carpentier |
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,860,951 A | 1/1999 | Eggers et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,283,961 B1 | 9/2001 | Underwood et al. |
| 6,296,656 B1 | 10/2001 | Bolduc et al. |
| 6,306,163 B1 | 10/2001 | Fitz |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,575,971 B2 | 6/2003 | Hauck et al. |
| 6,579,297 B2 | 6/2003 | Bicek et al. |
| 6,589,160 B2 | 7/2003 | Schweich, Jr. et al. |

(56) References Cited

U.S. PATENT DOCUMENTS

| | | |
|---|---|---|
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,656,221 B2 | 12/2003 | Taylor et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,716,243 B1 | 4/2004 | Colvin et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |

(56) References Cited

U.S. PATENT DOCUMENTS

| | | |
|---|---|---|
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0095175 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |

(56) References Cited

U.S. PATENT DOCUMENTS

| | | |
|---|---|---|
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0073302 A1 | 4/2004 | Rourke et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0220610 A1 | 11/2004 | Kreidler et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070924 A1 | 3/2005 | Schaller et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216078 A1 | 9/2005 | Starksen et al. |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0058817 A1 | 3/2006 | Starksen et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0129188 A1 | 6/2006 | Starksen et al. |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |

(56) References Cited

U.S. PATENT DOCUMENTS

| | | |
|---|---|---|
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0051823 A1 | 2/2008 | Makower et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1* | 7/2008 | Starksen ............ A61B 17/064 623/2.11 |
| 2008/0177382 A1 | 7/2008 | Hyde et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0243150 A1 | 10/2008 | Starksen et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076597 A1 | 3/2009 | Dahlgren et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0093890 A1 | 4/2009 | Gelbart |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0177277 A1* | 7/2009 | Milo ................... A61F 2/2445 623/2.36 |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0076549 A1 | 3/2010 | Keldar et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1* | 10/2010 | Annest ............ A61B 17/0469 623/2.17 |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |

(56) References Cited

U.S. PATENT DOCUMENTS

| | | |
|---|---|---|
| 2011/0087146 A1 | 4/2011 | Ryan et al. |
| 2011/0093002 A1 | 4/2011 | Rucker et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0257728 A1 | 10/2011 | Kuehn |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2011/0301701 A1 | 12/2011 | Padala et al. |
| 2012/0010700 A1 | 1/2012 | Spenser |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |

(56) References Cited

U.S. PATENT DOCUMENTS

| | | |
|---|---|---|
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |

FOREIGN PATENT DOCUMENTS

| | | | |
|---|---|---|---|
| CN | 102215784 | A | 10/2011 |
| CN | 113331995 | A | 9/2021 |
| EP | 1034753 | A1 | 9/2000 |
| EP | 3551975 | A1 | 9/2019 |
| JP | 2007514455 | A | 6/2007 |
| JP | 2009507532 | A | 2/2009 |
| JP | 2010511469 | A | 4/2010 |
| JP | 2012521222 | A | 9/2012 |
| WO | 9205093 | A1 | 4/1992 |
| WO | 9846149 | A1 | 10/1998 |
| WO | 02085250 | A3 | 2/2003 |
| WO | 03047467 | A1 | 6/2003 |
| WO | 2005025644 | A2 | 3/2005 |
| WO | 2006052687 | A1 | 5/2006 |
| WO | 2007098512 | A1 | 9/2007 |
| WO | 2008068756 | A2 | 6/2008 |
| WO | 2009120764 | A2 | 10/2009 |
| WO | 2010000454 | A1 | 1/2010 |
| WO | 2010091383 | A2 | 8/2010 |
| WO | 2010108079 | A1 | 9/2010 |
| WO | 2012084714 | A2 | 6/2012 |
| WO | 2012176195 | A3 | 3/2013 |
| WO | 2013088327 | A1 | 6/2013 |
| WO | 2014064964 | A1 | 5/2014 |
| WO | 2019145941 | A1 | 8/2019 |
| WO | 2019145947 | A1 | 8/2019 |
| WO | 2019182645 | A1 | 9/2019 |
| WO | 2019224814 | A1 | 11/2019 |
| WO | 2020240282 | A2 | 12/2020 |
| WO | 2021014440 | A2 | 1/2021 |
| WO | 2021038559 | A1 | 3/2021 |
| WO | 2021038560 | A1 | 3/2021 |
| WO | 2022064401 | A2 | 3/2022 |
| WO | 2022090907 | A1 | 5/2022 |
| WO | 2022101817 | A2 | 5/2022 |
| WO | 2022153131 | A1 | 7/2022 |
| WO | 2022157592 | A1 | 7/2022 |
| WO | 2022172108 | A1 | 8/2022 |
| WO | 2022172149 | A1 | 8/2022 |
| WO | 2022200972 | A1 | 9/2022 |
| WO | 2022224071 | A1 | 10/2022 |
| WO | 2022229815 | A1 | 11/2022 |
| WO | 2022250983 | A1 | 12/2022 |

OTHER PUBLICATIONS

Daimon, et al., "Percutaneous Mitral Valve Repair for Chronic Ischemic Mitral Regurgitation." Journal of the American Heart Association, publ. Apr. 25, 2005.

Desimone, et al., "Adjustable Tricuspid Valve Annuloplasty Assisted by Intraoperative Transesophageal." The American Journal of Cardiology vol. 71 pp. 926-931 Apr. 15, 1993.

Felger, M.D., et al., "Robot-assisted Sutureless Minimally Invasive Mitral Valve Repair", Cardiovascular Surgery, Surgical Technology International XII, p. 185-187 (undated).

Folliguet, et al., "Mitral valve repair robotic versus stemotomy" European Journal of Cardio-Thoracic Surgery 29 (2006) pp. 362-366.

Greelish et al., "Minimally invasive mitral valve repair suggests earlier operations for mitral valve," The Journal of thoracic & Cardiovascular Surgery vol. 126, No. 2 (2003).

International Search Report and Written Opinion for application No. PCT/US2016/014397 dated May 9, 2016.

International Search Report and Written Opinion for International Application No. PCT/IB2014/000949 dated Jan. 20, 2015.

International Search Report and Written Opinion in corresponding application PCT/IB2012/057138, 14 pages, Feb. 28, 2013.

Maniu, MD, et al. :Acute & Chronic Reduction of Functional Mitral Regurgitation Journal of Merican College of Cardiology, vol. 44, No. 8, pp. 1652-1661 (2004).

Notice of Allowance dated Oct. 16, 2018 (Heisei 30) in counterpart Japanese application No. JP 2016-517696 citing JP 2009-507532.

Office Action for Japanese Patent Application No. 2014-545447 dated Oct. 31, 2016 (includes English language translation).

Office Action for U.S. Appl. No. 14/364,060 dated Nov. 23, 2016.

Office Action dated Aug. 18, 2017, in Chinese Patent Application 201610004737.X.

Office Action issued in Japanese application No. JP 2016-517696 dated Feb. 19, 2018.

Agarwal et al. International Cardiology Perspective Functional Tricuspid Regurgitation, Circ Cardiovasc Interv 2009;2;2;565-573 (2009).

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

(56) References Cited

OTHER PUBLICATIONS

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results o4yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

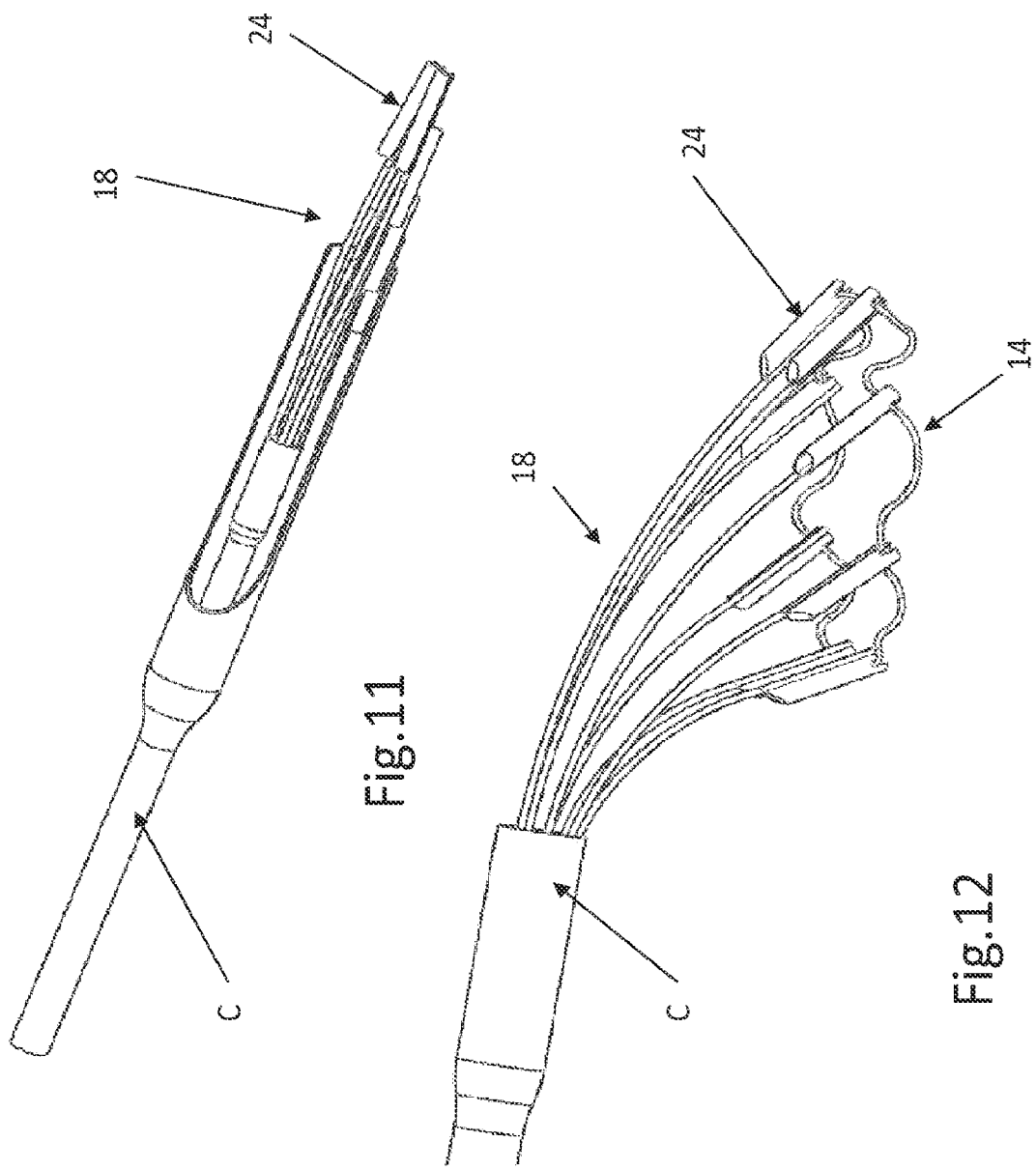

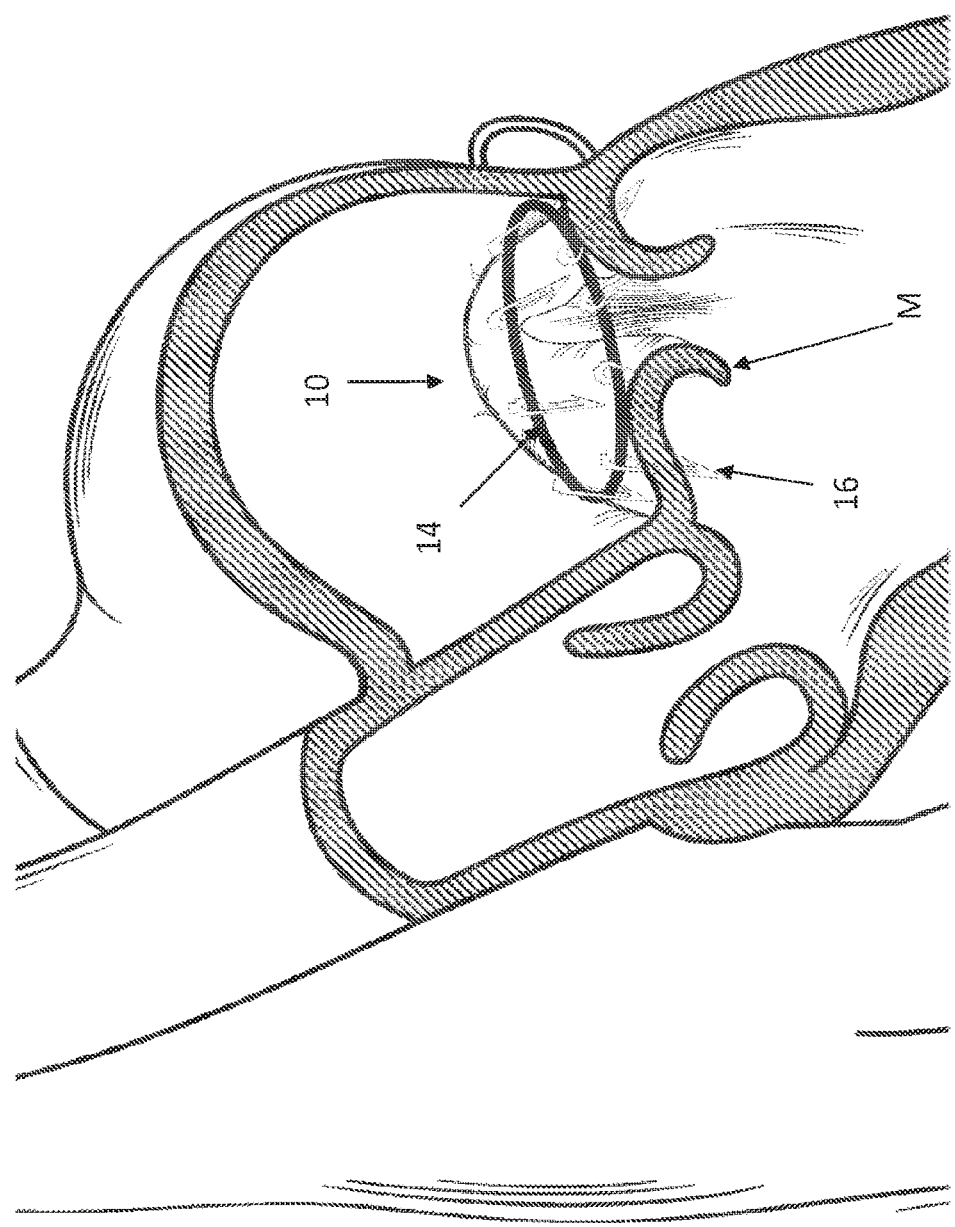

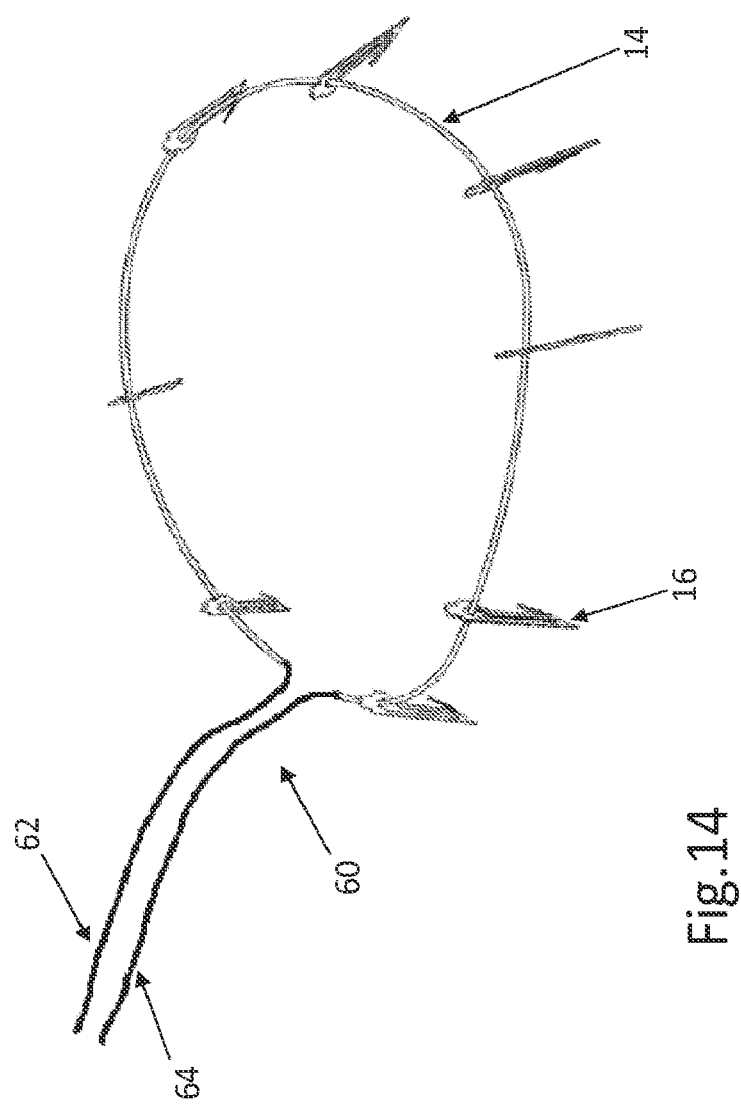

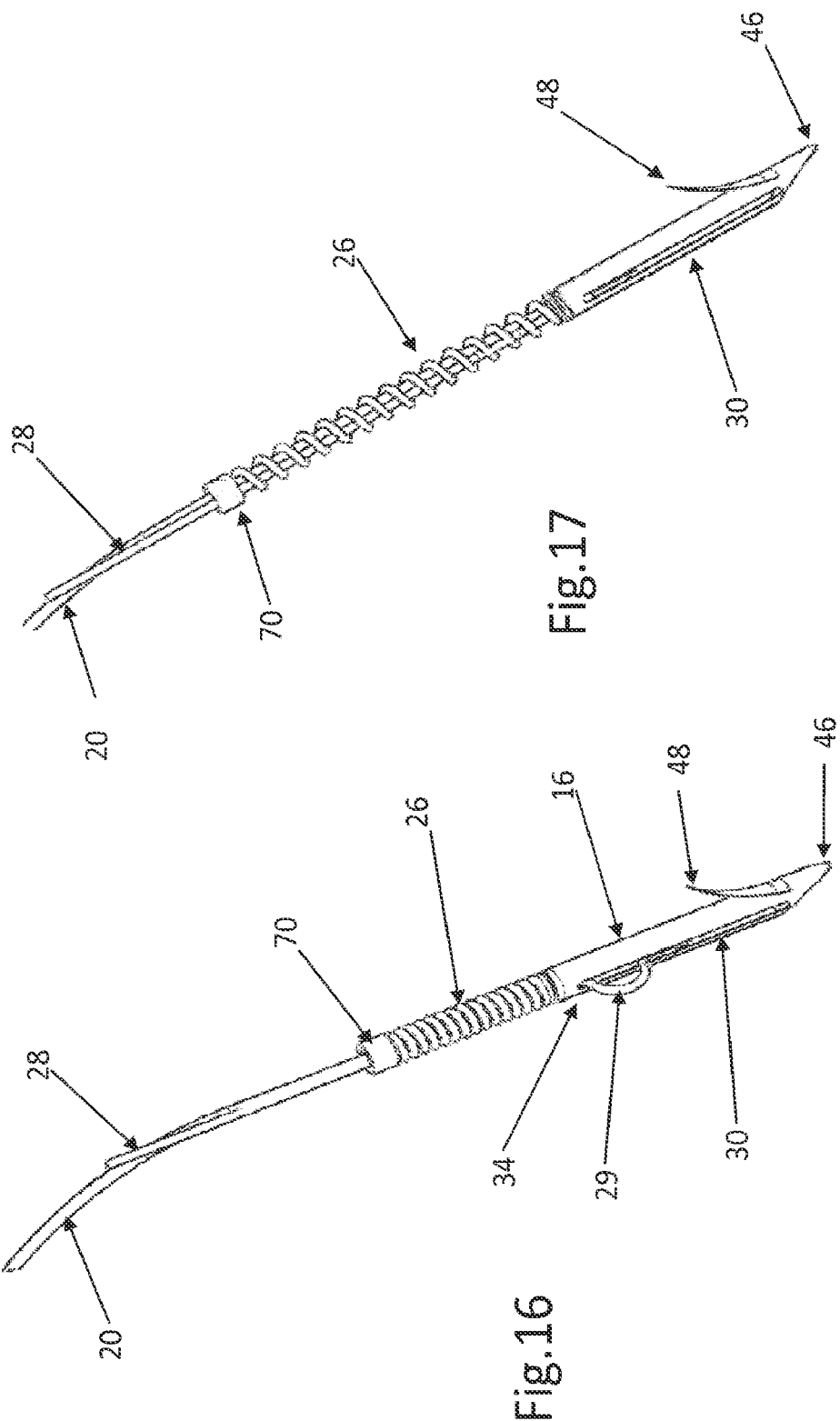

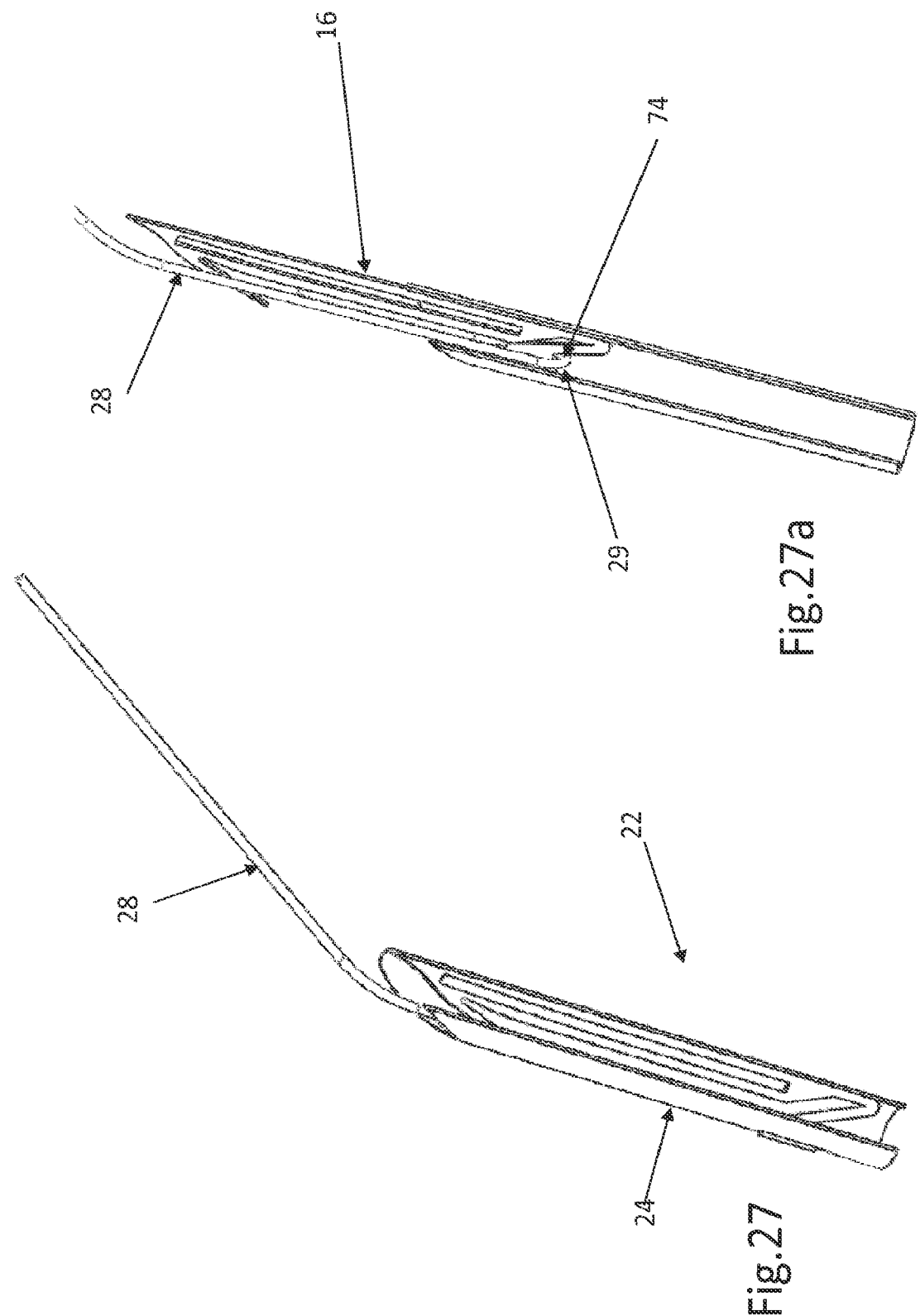

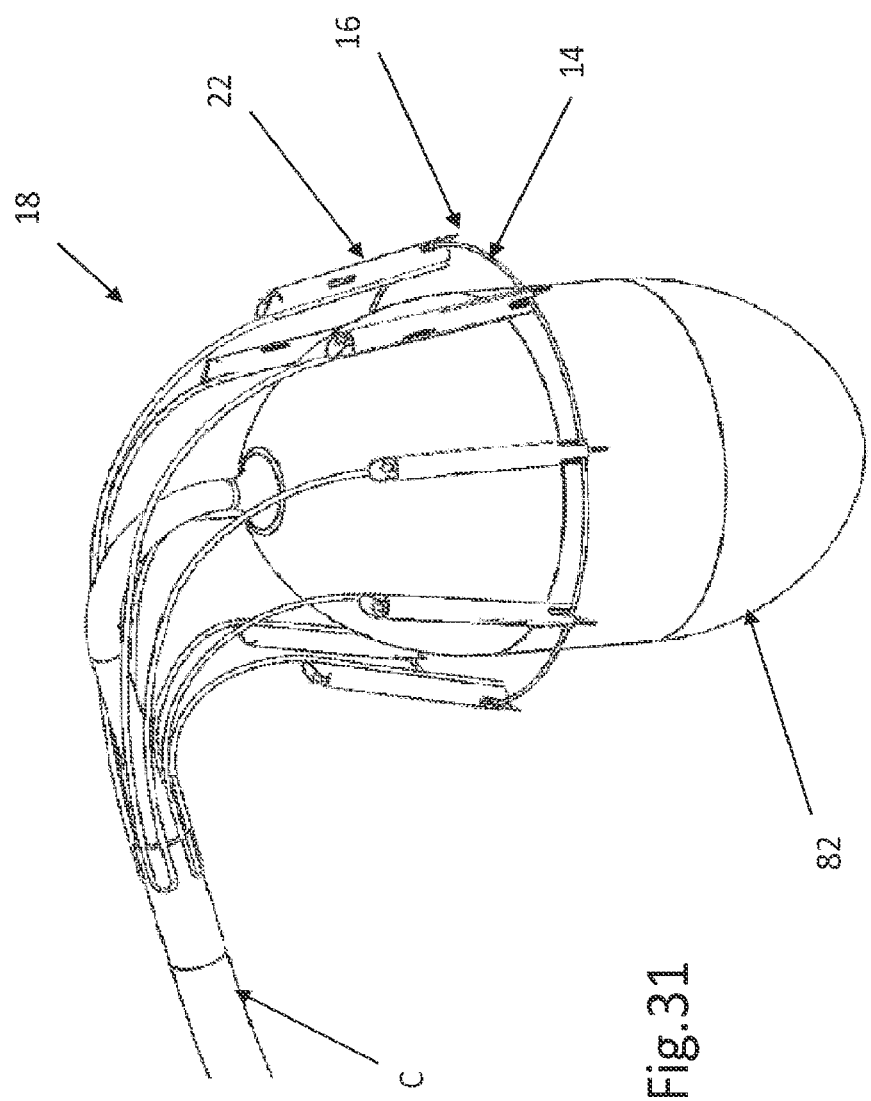

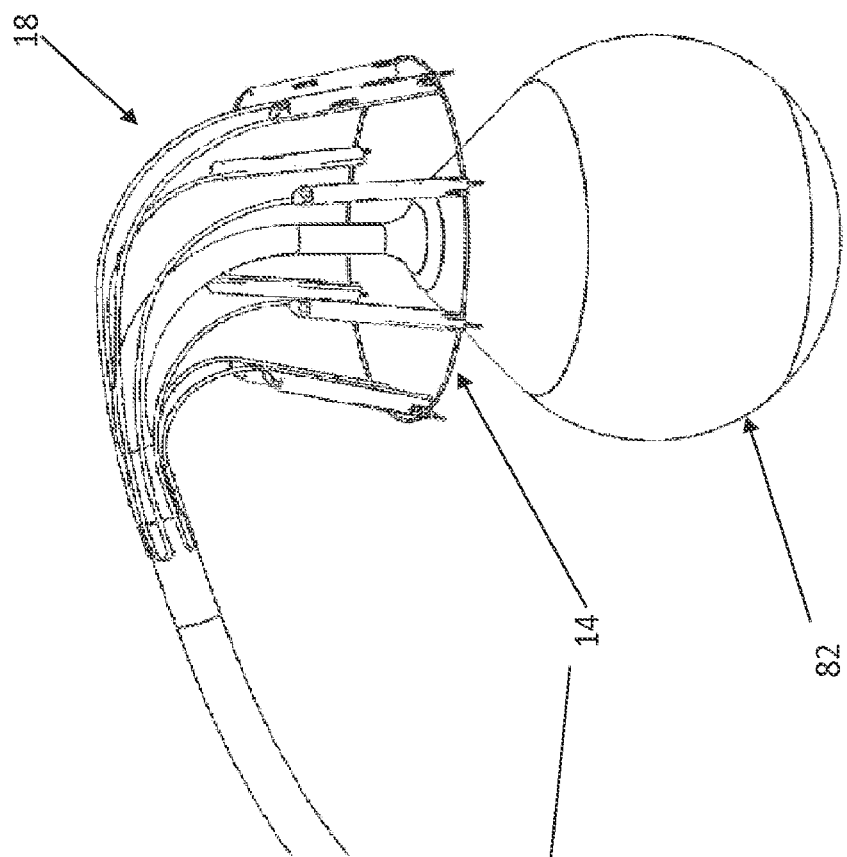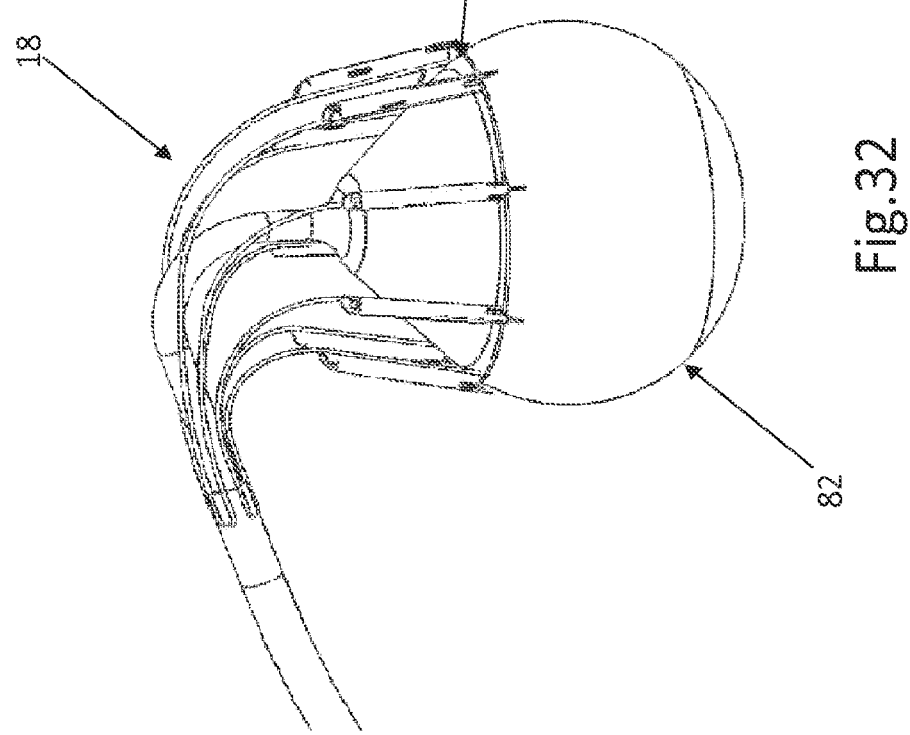

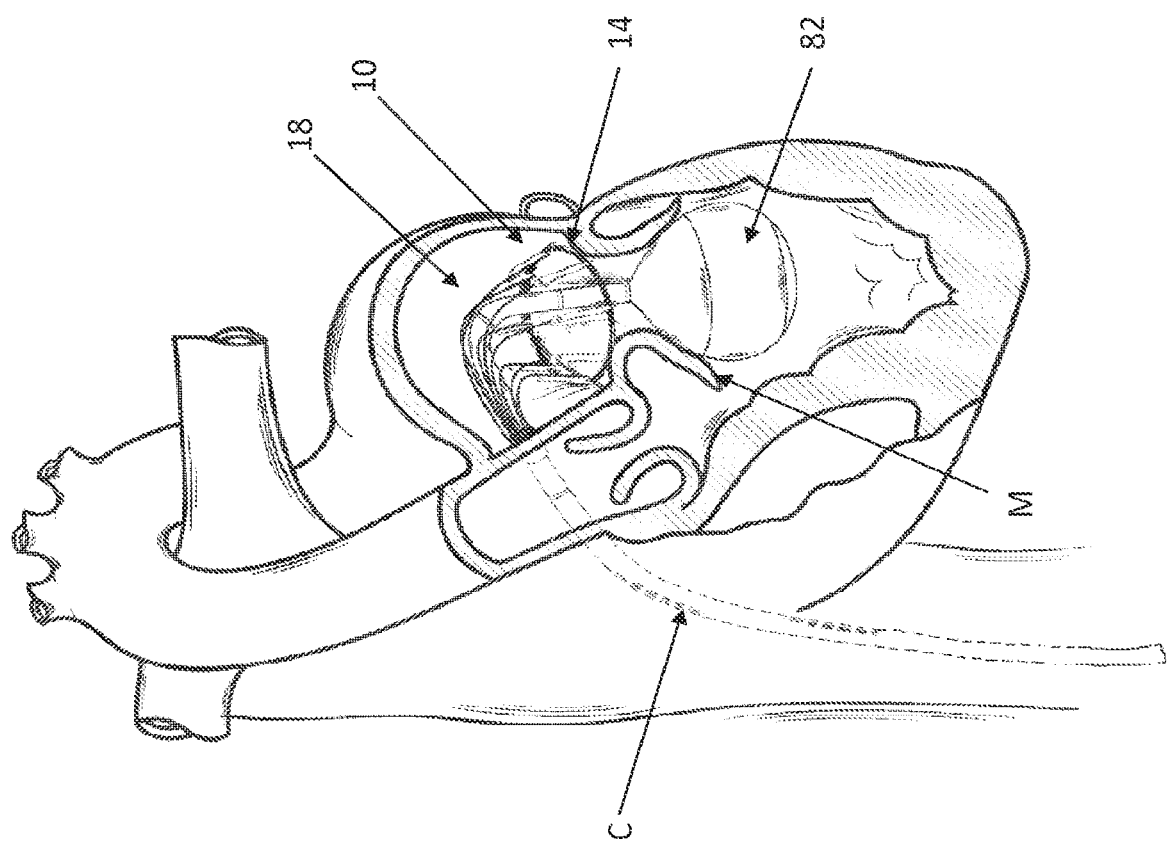

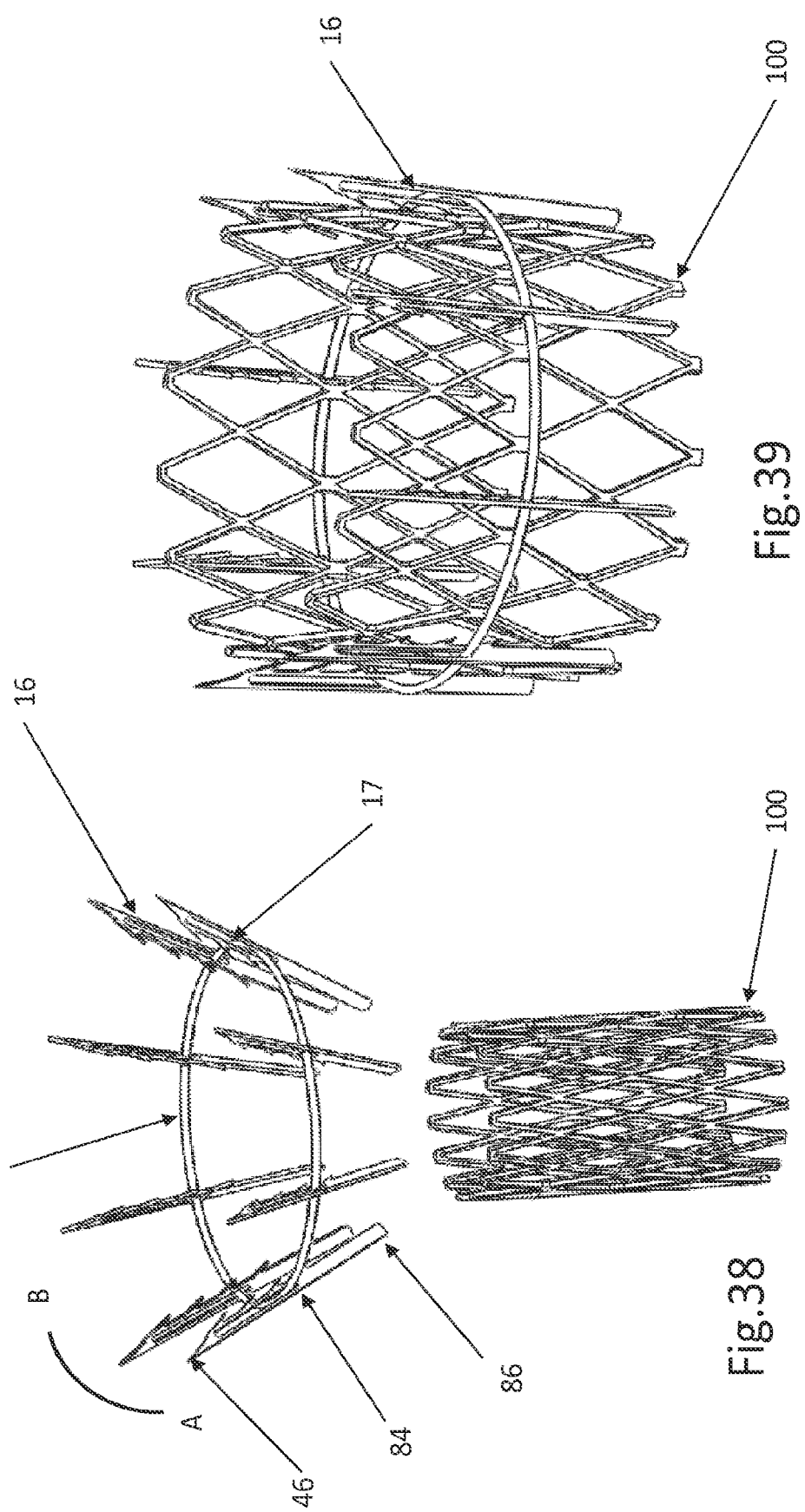

CARDIAC VALVE REPLACEMENT

CROSS REFERENCE TO RELATED APPLICATIONS

This application is a divisional of U.S. patent application Ser. No. 16/158,575, filed Oct. 12, 2018, which is a continuation of U.S. patent application Ser. No. 14/364,060, filed Jun. 9, 2014, which is a national stage application under 35 U.S.C. § 371 of PCT/IB2012/057138, filed Dec. 10, 2012, which published as WO 2013/088327 and claims the benefit of U.S. Provisional Application 61/683,736, filed Aug. 16, 2012, and U.S. Provisional Application 61/569,304, filed Dec. 12, 2011. Each of the above-identified applications is incorporated herein by reference.

FIELD OF THE INVENTION

The present invention relates to medical devices, in particular, devices for repairing biological valves.

BACKGROUND OF THE INVENTION

The mitral valve is positioned in the heart left side, between the left atrium and the left ventricle. The most typical disease of the mitral valve is insufficiency or regurgitation which occurs when the valve leaflets do not coapt properly. Mitral valve repair by suturing a ring to reduce the annulus diameter is the procedure of choice to correct mitral regurgitation. With the use of current surgical techniques, most regurgitant mitral valves can be repaired or replaced with artificial valve prosthesis.

Currently, mitral valve repair requires an extremely invasive surgical approach that includes a sternotomy, cardiopulmonary bypass, cardiac arrest, and an incision in the heart itself to expose the mitral valve. Such procedure is associated with high morbidity and mortality. A percutaneous device that can effectively treat the disease without the need for open heart surgery could greatly improve patient benefit and may include other patients that currently cannot be treated with surgery being too old or frail for such invasive procedure.

Most current surgical practices for mitral valve repair involve mitral valve annuloplasty and/or mitral valve valvuloplasty.

Surgical annuloplasty is a technique aimed to reduce the size of the fibrous tissue at the base of the mitral valve, called the annulus. Sometimes the annulus becomes enlarged, enabling blood to back flow up into the left atrium, through the gap between the two separated valve leaflets. The repair is done with sutures to make the opening smaller, helping the two leaflets meet and co-apt again when the valve closes.

Surgical valvuloplasty is a technique aimed to ensure proper closure of the valve leaflets. Leaflet function can be impaired as the result of prolapse of a leaflet due to ruptured chordae. The leaflet reconstruction is done by leaflet resection and reshaped with sutures. In most cases both annuloplasty and valvuloplasty is needed in order to regain optimal mitral valve function.

Due to the invasive nature of the mitral valve surgery, and the high risks involved in the procedure, many heart failure patients are poor surgical candidates. Thus, less invasive methods and devices to reduce mitral valve regurgitation would make this therapy available to many more patients.

US2004/102839, US2004/1022840, U.S. Pat. Nos. 6,656,221, 6,718,985, 6,723,038 and US2004/073302 describe minimal invasive approaches to mitral valve annuloplasty, using percutaneous insertion of device into the left ventricle or into the coronary sinus, in order to decrease the annulus size.

U.S. Pat. Nos. 6,626,930 and 6,575,971 disclose a device and method of fastening two pieces of the valve leaflets together, improving competence of the valve.

US2004/243227, US2007/244554, US2008/262609, and US2009/0287304 describe percutaneous devices which attach to the valve annulus via anchoring mechanisms and contract, thereby reducing annulus diameter in a single step.

US2007/016286 discloses a transluminal collapsible heart valve designed to attach to the native annulus of the native regurgitating mitral valve and replace all in a single step. US2012/010700 provides a method for implanting a prosthetic valve apparatus that includes a one way valve and an expandable valve seating. The apparatus is anchored and secured in a newly created orifice near or at the center of the anterior valve leaflet.

Today it is possible to replace an aortic valve (the valve positioned between the left ventricle and aorta) with no surgery through newly developed percutaneous procedures. In these procedures an artificial collapsed valve is delivered through the arteries and positioned inside the diseased native valve, and then expanded to replace it. To date there is yet no acceptable analogous procedure that can do the same for the mitral or tricuspid valves.

Following the success of percutaneous replacement of the aortic valve, many attempts have been made to develop similar devices intended for percutaneous treatment of the mitral valve but due to the fact that this valve annulus is much bigger and amorphously shaped, and there are no lumen walls or calcific leaflets that may function as retaining surfaces like in the aortic valve, make it very difficult to prevent dislodgment of a valve expanded into place in the mitral position. Attaching a valve to the mitral annulus with anchoring features is very challenging for a percutaneous procedure and has not been very successful yet.

Devices that are attached to the mitral annulus and then collapsed to reduce its diameter need to be secured very tightly and accurately to the tissue in order to withhold the high forces that are required to reduce the annulus diameter.

Compared to the aortic valve percutaneous procedures, all the devices and procedures mentioned above have not been successful for the mitral valve yet.

SUMMARY OF THE INVENTION

The present invention relates to a device, method and kit for helping repair a biological valve and is particularly suited for repair of mitral, tricuspid and such valves, though not necessarily limited to such implementations.

In accordance with embodiments of one aspect of the invention there is provided an apparatus for performing a procedure on a heart valve annulus, the heart valve annulus having an original shape, the apparatus comprising: a tissue engaging member including a loop of wire configured to conform with at least a portion of the original shape when the loop of wire is deployed, and a plurality of anchors, each of the plurality of anchors having a pointy front end and a back end, each of the plurality of anchors having a slot that runs in a front-to-back direction, wherein the front ends of the plurality of anchors are configured for implantation into heart valve annulus tissue in a forward direction and wherein the plurality of anchors are configured so that subsequent to implantation, the plurality of anchors resist extraction from the heart valve annulus tissue in a backwards direction, wherein the plurality of anchors are arranged with respect to the loop of wire so that when the loop of wire is deployed the plurality of anchors are distributed about the loop of wire with the front ends of the plurality of anchors facing the heart valve annulus and with the loop of wire passing through the slots in the plurality of anchors. The apparatus further includes means for implanting the plurality of anchors into the heart valve annulus tissue so that the tissue engaging member becomes affixed to the heart valve annulus.

In some embodiments, the loop of wire comprises a closed loop. In some embodiments, the at least a portion of the original shape comprises at least a 270° portion of the original shape. In some embodiments, each of the plurality of anchors includes a barb that, subsequent to implantation, resists extraction from the heart valve annulus tissue in a backwards direction. In some embodiments, each of the plurality of anchors the back end of the slot is enlarged to form an eyelet. In some embodiments, in each of the plurality of anchors the slot begins near the front end of the anchor and ends near the back end of the anchor, and wherein, during implantation, forward motion of the plurality of anchors is limited when the ends of the slots encounter the loop of wire.

In some embodiments, the tissue engaging member further includes a plurality of tubes threaded onto the loop of wire between the plurality of anchors, wherein an outer surface of the tubes comprises a material that promotes tissue growth. In some embodiments, the tissue engaging member further includes a second loop of wire that is threaded through the inside the plurality of tubes, and wherein the second loop of wire comprises a closed loop.

In some embodiments, at least a portion of the second loop of wire is surrounded by a material that inhibits tissue growth. In some embodiments, the plurality of anchors comprises at least six anchors.

In some embodiments, the means for implanting comprises a plurality of compressed springs configured to, respectively, implant the plurality of anchors into the heart valve annulus tissue so that the tissue engaging member becomes affixed to the heart valve annulus. In some embodiments, the means for implanting comprises a plurality of pull wires configured to, respectively, implant the plurality of anchors into the heart valve annulus tissue so that the tissue engaging member becomes affixed to the heart valve annulus.

In some embodiments, the loop of wire comprises a closed loop, wherein each of the plurality of anchors includes a barb that, subsequent to implantation, resists extraction from the heart valve annulus tissue in a backwards direction, and wherein the plurality of anchors comprises at least six anchors. In some embodiments, the means for implanting comprises a plurality of compressed springs configured to, respectively, implant the plurality of anchors into the heart valve annulus tissue so that the tissue engaging member becomes affixed to the heart valve annulus. In some embodiments, the means for implanting comprises a plurality of pull wires configured to, respectively, implant the plurality of anchors into the heart valve annulus tissue so that the tissue engaging member becomes affixed to the heart valve annulus.

In some embodiments, the apparatus further comprises a catheter having a distal end; and a scaffold comprising a plurality of support arms configured to support the plurality of anchors in position adjacent to the heart valve annulus in a position at which the means for implanting can implant the plurality of anchors into the heart valve annulus tissue.

In some embodiments, the heart valve annulus is a mitral valve annulus, and the apparatus further comprises: a catheter having a distal end; and a scaffold comprising a plurality of support arms, wherein the scaffold is configured for deployment when the distal end of the catheter is positioned in the left atrium and the scaffold is further configured to support the plurality of anchors in position adjacent to the upper surface of the mitral valve annulus in a position at which the means for implanting can implant the plurality of anchors into the mitral valve annulus, wherein the catheter is configured to push the plurality of anchors towards the upper surface of the mitral valve annulus prior to implanting of the plurality of anchors.

In some embodiments, the apparatus further comprises a balloon configured for delivery in a deflated state via the catheter, and configured for inflation while at least part of the balloon is positioned the left ventricle, and wherein the catheter is configured to pull the balloon towards the mitral valve annulus prior to implanting of the plurality of anchors.

In some embodiments, the apparatus further comprises a balloon configured for delivery in a deflated state via the catheter, wherein when the balloon is inflated, the balloon guides the tissue engaging member into position for implantation into the mitral valve annulus.

In accordance with embodiments of another aspect of the invention there is provided a method for performing a procedure on a heart valve annulus, the heart valve annulus having an original shape. The method comprises the steps of: delivering a loop of wire to the vicinity of heart valve annulus so that the loop of wire conforms with at least a portion of the original shape; delivering a plurality of anchors to the vicinity of heart valve annulus, each of the plurality of anchors having a pointy front end and a back end, each of the plurality of anchors having a slot that runs in a front-to-back direction, wherein the front ends of the plurality of anchors are configured for implantation into heart valve annulus tissue in a forward direction and wherein the plurality of anchors are configured so that subsequent to implantation, the plurality of anchors resist extraction from the heart valve annulus tissue in a backwards direction, wherein the plurality of anchors are distributed about the loop of wire with the front ends of the plurality of anchors facing the heart valve annulus and with the loop of wire passing through the slots in the plurality of anchors; and implanting the plurality of anchors into the heart valve annulus.

In some embodiments, the loop of wire comprises a closed loop. In some embodiments, the at least a portion of the original shape comprises at least a 270° portion of the original shape. In some embodiments, each of the plurality of anchors the slot begins near the front end of the anchor and ends near the back end of the anchor, and wherein, during the implanting step, forward motion of the plurality of anchors is limited when the ends of the slots encounter the loop of wire.

In some embodiments, the method further comprises the step of delivering a plurality of tubes to the vicinity of heart valve annulus, wherein the plurality of tubes are threaded onto the loop of wire between the plurality of anchors and wherein an outer surface of the tubes comprises a material that promotes tissue growth.

In some embodiments, the method further comprises the step of delivering a second loop of wire to the vicinity of heart valve annulus that is threaded through the inside the plurality of tubes, wherein the second loop of wire comprises a closed loop. In some embodiments, the plurality of anchors comprises at least six anchors.

In some embodiments, the implanting step comprises driving the plurality of anchors into the heart valve annulus using a plurality of springs. In some embodiments, the implanting step comprises driving the plurality of anchors into the heart valve annulus using a plurality of pull wires. In some embodiments, the heart valve annulus is a mitral valve annulus, and the method further comprises the step of pressing the plurality of anchors towards an upper surface of the mitral valve annulus, wherein the pressing step is implemented prior to the implanting step and subsequent to the steps of delivering the loop of wire and delivering the plurality of anchors.

In some embodiments, the method further comprises the step of pulling an inflated balloon that is disposed at least partially in a left ventricle towards the mitral valve annulus, wherein the pulling step and the pressing step are performed simultaneously. In some embodiments, the method further comprises the step of inflating a balloon to guide the anchors into position for implantation into the mitral valve annulus.

In accordance with embodiments of another aspect of the invention there is provided an apparatus for performing a procedure on a mitral valve, the apparatus comprising: a tissue engaging member including a loop of wire configured to contact leaflets of the mitral valve when the loop of wire is deployed, wherein the loop of wire comprises a closed loop, and a plurality of anchors, each of the plurality of anchors having a pointy front end and a back end, each of the plurality of anchors having a slot that runs in a front-to-back direction, wherein the front ends of the plurality of anchors are configured for implantation into the leaflets in a forward direction and wherein the plurality of anchors are configured so that subsequent to implantation, the plurality of anchors resist extraction from the leaflets in a backwards direction, wherein the plurality of anchors are arranged with respect to the loop of wire so that when the loop of wire is deployed the plurality of anchors are distributed about the loop of wire with the front ends of the plurality of anchors facing the leaflets and with the loop of wire passing through the slots in the plurality of anchors. The apparatus further includes means for implanting the plurality of anchors into the leaflets so that the tissue engaging member becomes affixed to the leaflets.

In some embodiments, each of the plurality of anchors includes a barb that, subsequent to implantation, resists extraction from the leaflets in a backwards direction. In some embodiments, each of the plurality of anchors the slot begins near the front end of the anchor and ends about halfway between the front end of the anchor and the back end of the anchor, and during implantation, forward motion of the plurality of anchors is limited when the ends of the slots encounter the loop of wire.

In some embodiments, the plurality of anchors comprises at least six anchors. In some embodiments, the means for implanting comprises a plurality of compressed springs configured to, respectively, implant the plurality of anchors into the leaflets so that the tissue engaging member becomes affixed to the leaflets.

In some embodiments, the means for implanting comprises a plurality of pull wires configured to, respectively, implant the plurality of anchors into the leaflets so that the tissue engaging member becomes affixed to the leaflets.

In some embodiments, the apparatus further comprises a catheter having a distal end; and a scaffold comprising a plurality of support arms configured to support the plurality of anchors in position adjacent to the leaflets in a position at which the means for implanting can implant the plurality of anchors into the leaflets.

In some embodiments, the apparatus further comprises: a catheter having a distal end; and a scaffold comprising a plurality of support arms, wherein the scaffold is configured for deployment when the distal end of the catheter is positioned in the left ventricle and the scaffold is further configured to support the plurality of anchors in position adjacent to the leaflets in a position at which the means for implanting can implant the plurality of anchors into the leaflets, wherein the catheter is configured to push the plurality of anchors towards the leaflets prior to implanting of the plurality of anchors.

In some embodiments, the apparatus further comprises: a catheter having a distal end; and a scaffold comprising a plurality of support arms, wherein the scaffold is configured for deployment when the distal end of the catheter is positioned in the left ventricle and the scaffold is further configured to support the plurality of anchors in position adjacent to the leaflets in a position at which the means for implanting can implant the plurality of anchors into the leaflets, wherein the catheter is configured to pull the plurality of anchors towards the leaflets prior to implanting of the plurality of anchors.

In accordance with embodiments of another aspect of the invention there is provided a method for performing a procedure on a mitral valve comprising the steps of: delivering a loop of wire to a vicinity of leaflets of the mitral valve, wherein the loop of wire comprises a closed loop; delivering a plurality of anchors to the vicinity of the leaflets, each of the plurality of anchors having a pointy front end and a back end, each of the plurality of anchors having a slot that runs in a front-to-back direction, wherein the front ends of the plurality of anchors are configured for implantation into the leaflets in a forward direction and wherein the plurality of anchors are configured so that subsequent to implantation, the plurality of anchors resist extraction from the leaflets in a backwards direction, wherein the plurality of anchors are distributed about the loop of wire with the front ends of the plurality of anchors facing the leaflets and with the loop of wire passing through the slots in the plurality of anchors; and implanting the plurality of anchors into the leaflets.

In some embodiments, each of the plurality of anchors the slot begins near the front end of the anchor and ends about halfway between the front end of the anchor and the back end of the anchor, and wherein, during the implanting step, forward motion of the plurality of anchors is limited when the ends of the slots encounter the loop of wire.

In some embodiments, the plurality of anchors comprises at least six anchors. In some embodiments, the implanting step comprises driving the plurality of anchors into the leaflets using a plurality of springs. In some embodiments, the implanting step comprises driving the plurality of anchors into the leaflets using a plurality of pull wires.

In some embodiments, the method further comprises the step of pressing the plurality of anchors towards the leaflets, wherein the pressing step is implemented prior to the implanting step and subsequent to the steps of delivering the loop of wire and delivering the plurality of anchors.

In accordance with embodiments of another aspect of the invention there is provided an apparatus for cinching a heart valve annulus, the heart valve annulus having an original shape, the apparatus comprising: a tissue engaging member including a first loop of wire configured to conform with at least a portion of the original shape when the first loop of wire is deployed, a plurality of anchors, each of the plurality of anchors having a pointy front end and a back end, each of the plurality of anchors having a slot that runs in a front-to-back direction, wherein the front ends of the plurality of anchors are configured for implantation into heart valve annulus tissue in a forward direction and wherein the plurality of anchors are configured so that subsequent to implantation, the plurality of anchors resist extraction from the heart valve annulus tissue in a backwards direction, wherein the plurality of anchors are arranged with respect to the first loop of wire so that when the first loop of wire is deployed the plurality of anchors are distributed about the first loop of wire with the front ends of the plurality of anchors facing the heart valve annulus and with the first loop of wire passing through the slots in the plurality of anchors, a plurality of tubes threaded onto the first loop of wire between the plurality of anchors, wherein an outer surface of the tubes comprises a material that promotes tissue growth, and a second loop of wire that is threaded through the inside the plurality of tubes, the second loop of wire having two ends that are configured so that when the tissue engaging member is affixed to the heart valve annulus, pulling the two ends will cinch the heart valve annulus; and means for implanting the plurality of anchors into the heart valve annulus tissue so that the tissue engaging member becomes affixed to the heart valve annulus.

In some embodiments, at least a portion of the second loop of wire is surrounded by a material that inhibits tissue growth. In some embodiments, the at least a portion of the original shape comprises at least a 270° portion of the original shape. In some embodiments, wherein each of the plurality of anchors includes a barb that, subsequent to implantation, resists extraction from the heart valve annulus tissue in a backwards direction. In some embodiments, in each of the plurality of anchors the back end of the slot is enlarged to form an eyelet. In some embodiments, each of the plurality of anchors the slot begins near the front end of the anchor and ends near the back end of the anchor, and wherein, during implantation, forward motion of the plurality of anchors is limited when the ends of the slots encounter the first loop of wire.

In some embodiments, the plurality of anchors comprises at least six anchors. In some embodiments, the means for implanting comprises a plurality of compressed springs configured to, respectively, implant the plurality of anchors into the heart valve annulus tissue so that the tissue engaging member becomes affixed to the heart valve annulus. In some embodiments, the means for implanting comprises a plurality of pull wires configured to, respectively, implant the plurality of anchors into the heart valve annulus tissue so that the tissue engaging member becomes affixed to the heart valve annulus.

In some embodiments, each of the plurality of anchors includes a barb that, subsequent to implantation, resists extraction from the heart valve annulus tissue in a backwards direction, wherein the plurality of anchors comprises at least six anchors, and wherein the means for implanting comprises a plurality of compressed springs configured to, respectively, implant the plurality of anchors into the heart valve annulus tissue so that the tissue engaging member becomes affixed to the heart valve annulus. In some embodiments, each of the plurality of anchors includes a barb that, subsequent to implantation, resists extraction from the heart valve annulus tissue in a backwards direction, wherein the plurality of anchors comprises at least six anchors, and wherein the means for implanting comprises a plurality of pull wires configured to, respectively, implant the plurality of anchors into the heart valve annulus tissue so that the tissue engaging member becomes affixed to the heart valve annulus.

In some embodiments, the apparatus further comprises: a catheter having a distal end; and a scaffold comprising a plurality of support arms configured to support the plurality of anchors in position adjacent to the heart valve annulus in a position at which the means for implanting can implant the plurality of anchors into the heart valve annulus tissue.

In some embodiments, the heart valve annulus is a mitral valve annulus, and the apparatus further comprises: a catheter having a distal end; and a scaffold comprising a plurality of support arms, wherein the scaffold is configured for deployment when the distal end of the catheter is positioned in the left atrium and the scaffold is further configured to support the plurality of anchors in position adjacent to the upper surface of the mitral valve annulus in a position at which the means for implanting can implant the plurality of anchors into the mitral valve annulus, wherein the catheter is configured to push the plurality of anchors towards the upper surface of the mitral valve annulus prior to implanting of the plurality of anchors.

In some embodiments, the apparatus further comprises a balloon configured for delivery in a deflated state via the catheter, and configured for inflation while at least part of the balloon is positioned the left ventricle, and wherein the catheter is configured to pull the balloon towards the mitral valve annulus prior to implanting of the plurality of anchors.

In some embodiments, the apparatus further comprises a balloon configured for delivery in a deflated state via the catheter, wherein when the balloon is inflated, the balloon guides the tissue engaging member into position for implantation into the mitral valve annulus.

In accordance with embodiments of another aspect of the invention there is provided a method for cinching a heart valve annulus, the heart valve annulus having an original shape. The method comprising the steps of: delivering a first loop of wire to the vicinity of heart valve annulus so that the first loop of wire conforms with at least a portion of the original shape; delivering a plurality of anchors to the vicinity of heart valve annulus, each of the plurality of anchors having a pointy front end and a back end, each of the plurality of anchors having a slot that runs in a front-to-back direction, wherein the front ends of the plurality of anchors are configured for implantation into heart valve annulus tissue in a forward direction and wherein the plurality of anchors are configured so that subsequent to implantation, the plurality of anchors resist extraction from the heart valve annulus tissue in a backwards direction, wherein the plurality of anchors are distributed about the first loop of wire with the front ends of the plurality of anchors facing the heart valve annulus and with the first loop of wire passing through the slots in the plurality of anchors; delivering a plurality of tubes to the vicinity of heart valve annulus, wherein the plurality of tubes are threaded onto the first loop of wire between the plurality of anchors and wherein an outer surface of the tubes comprises a material that promotes tissue growth; delivering a second loop of wire to the vicinity of heart valve annulus, wherein the second loop of wire is threaded through the inside the plurality of tubes and has a first end and a second end; implanting the plurality of anchors into the heart valve annulus; and cinching the second loop of wire by pulling on the first end and the second end.

In some embodiments, the at least a portion of the original shape comprises at least a 270° portion of the original shape. In some embodiments, in each of the plurality of anchors the slot begins near the front end of the anchor and ends near the back end of the anchor, and wherein, during the implanting step, forward motion of the plurality of anchors is limited when the ends of the slots encounter the first loop of wire. In some embodiments, the plurality of anchors comprises at least six anchors.

In some embodiments, the implanting step comprises driving the plurality of anchors into the heart valve annulus using a plurality of springs. In some embodiments, the implanting step comprises driving the plurality of anchors into the heart valve annulus using a plurality of pull wires.

In some embodiments, the heart valve annulus is a mitral valve annulus, and the method further comprises the step of pressing the plurality of anchors towards an upper surface of the mitral valve annulus, wherein the pressing step is implemented prior to the implanting step and subsequent to the steps of delivering the first loop of wire and delivering the plurality of anchors.

In some embodiments, the method further comprising the step of pulling an inflated balloon that is disposed at least partially in a left ventricle towards the mitral valve annulus, wherein the pulling step and the pressing step are performed simultaneously.

In some embodiments, the method further comprises the step of inflating a balloon to guide the anchors into position for implantation into the mitral valve annulus.

BRIEF DESCRIPTION OF THE DRAWINGS

The present invention will be understood and appreciated more fully from the following detailed description taken in conjunction with the appended drawings in which:

FIGS. 11 and 12 are perspective views of an exemplary delivery system for the present device;

FIG. 13 is a front partially cut-away view of a heart with the implant affixed to a mitral valve from above the valve;

FIG. 14 is a perspective view of a cinching mechanism of the device;

FIGS. 15-17 are perspective views of additional embodiments of anchors;

FIGS. 23-27 and 27a are perspective views of further embodiments of anchor launching mechanisms;

FIGS. 31-34 show embodiments in which loop arrangement and/or implant positioning is implemented using an inflatable balloon;

FIGS. 35-39 are perspective views illustrating the device in use in conjunction with an implantable device;

Figure 1:
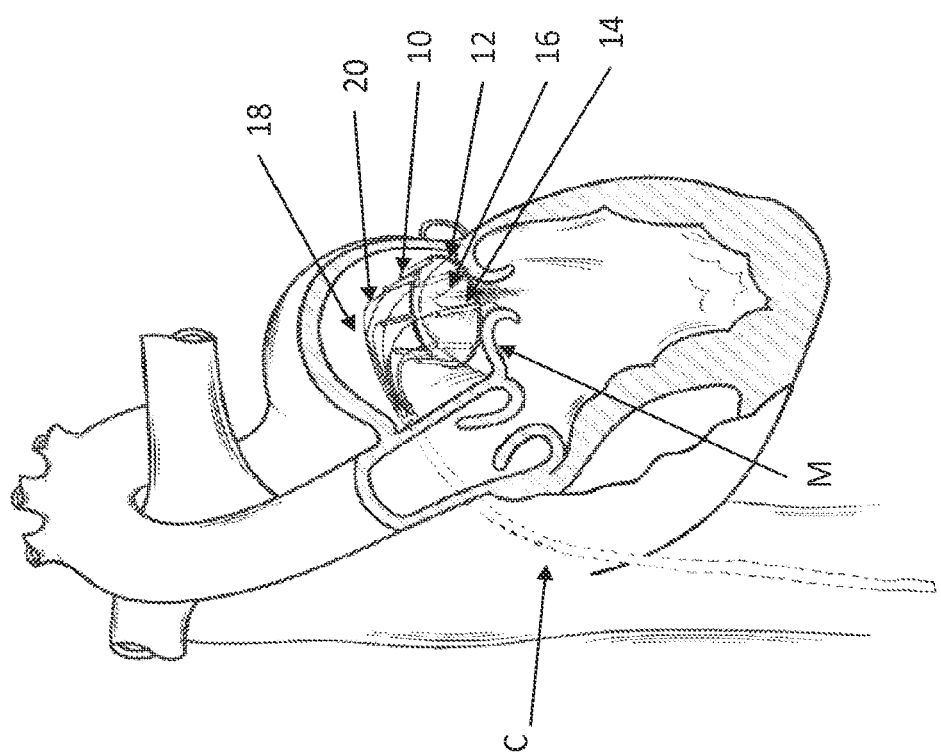
FIG. 1 is a front partial cut-away view of an embodiment of a heart valve repair device of the present invention.

The following detailed description of embodiments of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DESCRIPTION OF EMBODIMENTS OF THE INVENTION

A heart valve repair device comprising an implant and delivery system is delivered into the heart in four sequential stages: In the first stage the implant and support scaffold are advanced in a collapsed configuration inside a capsule through the vascular system to the valve annulus (preferably the Mitral annulus but can be also the Tricuspid annulus). In the second stage after positioning the capsule close to the annulus a support scaffold is pushed outside of the capsule and the implant which is attached to the scaffold is spread into a round or D shape circumferential ring onto the valve annulus in 3 optional ways:

1) On the inflow side of the valve with attachment anchors pointing from the atrium side to the ventricle side;
2) On the inflow side of the valve with attachment anchors pointing from the ventricle side to the atrium side; and
3) On the outflow side of the valve with attachment anchors pointing from the ventricle side to the atrium side.

In the third stage after the implant is spread out, all the anchors are launched into the tissue at once or in a sequential manner and affix the implant to the tissue. The same action also separates the implant from the support scaffold and delivery system. In the fourth stage the scaffold is retracted and collapsed back into the delivery capsule and the delivery system is withdrawn out of the body.

It is important to note that in some embodiments the spread implant conforms at least partially to the valve annulus shape, and in some embodiments the spread implant does not conform at all to the valve annulus shape, but is just affixed to the valve leaflets and is retained there for a few minutes until a valve prosthesis is deployed into it as will be described later on.

After the implant is attached to the valve tissue it is possible to treat the valve insufficiency in 5 optional ways:

1) By direct annuloplasty which impose cinching of the implant attached to the valve annulus, hence reducing the annulus diameter and improving valve leaflets coaptation;
2) By restricting annulus dilatation over time due to the constant perimeter of the implant which is attached to the valve annulus and gets embedded into the tissue over time through tissue growth;
3) By facilitating a support ring for valve prosthesis to be implanted at a later procedure after the implant which is attached to the valve annulus gets embedded into the tissue over time through tissue growth;
4) By performing annuloplasty at a later stage in a different procedure weeks or months later after the implant which is attached to the valve annulus gets embedded into the tissue over time through tissue growth; and 5) By facilitating a support ring for valve prosthesis that can be implanted into the ring during the same procedure right after the ring is attached to the valve leaflets.

Illustrative embodiments of the invention are described below. In the interest of clarity, not all features/components of an actual implementation are necessarily described.

FIG. 1 shows an embodiment of a mitral valve adjustment/repair implant 10 of the present invention, implanted onto a bio-valve, exemplified by mitral valve M of the heart. Implant 10 comprises: a tissue engaging member 12, comprising a loop 14 of wire and a plurality of tissue anchors 16 associated with the loop and having and an elongated slot 17 (FIG. 5); a scaffold or implant positioning device 18, in this embodiment comprising plurality of support arms 20; and an anchor launching mechanism 22 (FIGS. 2-7). Implant 10 is typically positioned in proximity of the mitral valve M via a delivery catheter C. The loop 14 of wire is preferably made of metal wire, but in alternative embodiments the wire may be a non-metallic material. Note that as used herein, "wire" includes metal and/or non-metallic materials.

Figure 2:
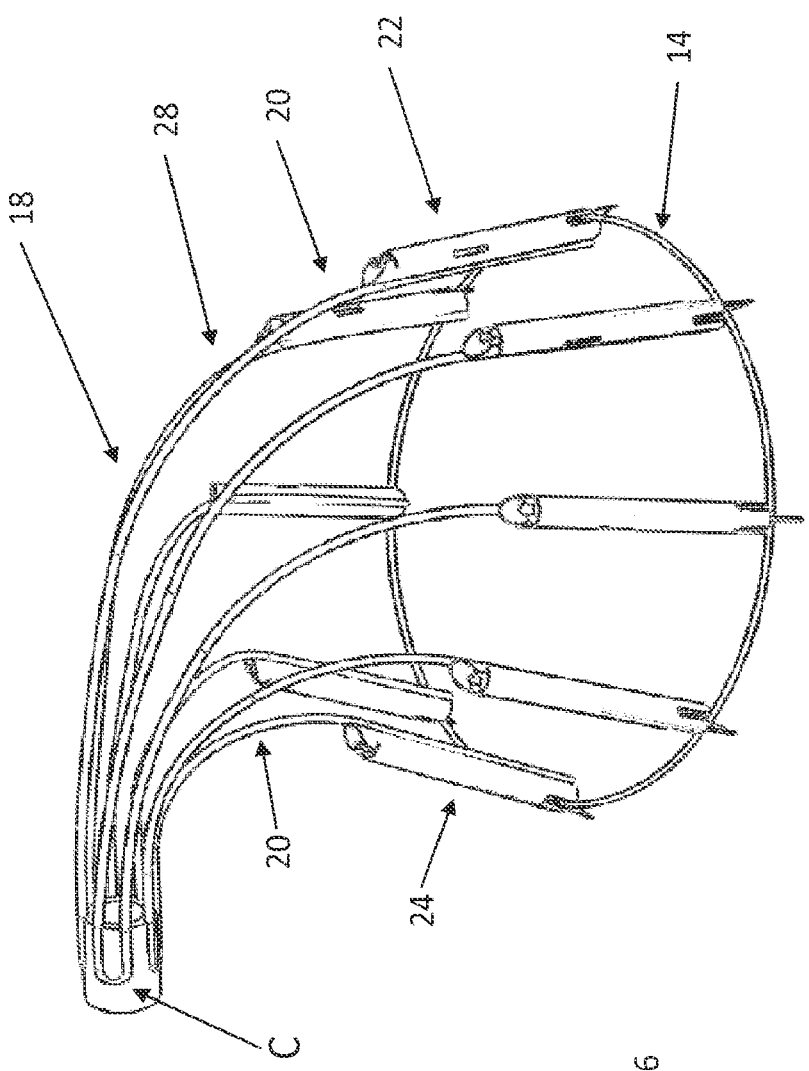
FIG. 2 is an enlarged perspective view of the device of FIG. 1.
Figure 3:
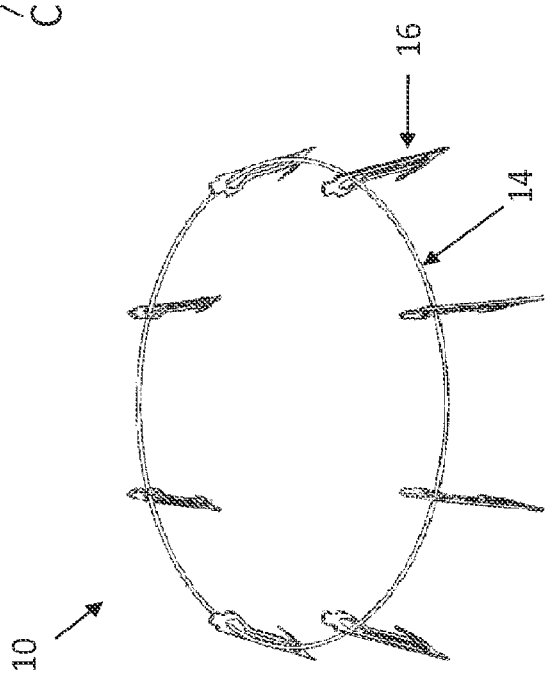
FIG. 3 is a perspective view of an implant or tissue engaging member of the present device.

FIG. 2 shows an enlarged view of the device in FIG. 1 illustrating anchor launching mechanism 22 in a ready for deployment (launching) and deployed state, respectively; Elongated slot 17 of anchors 16 allow loop 14 to be retained by (operably attached to) the anchors—which will be explained further herein below. FIG. 3 shows an embodiment of implant 10 in its configuration when implanted, as will be discussed further below.

Figure 5:
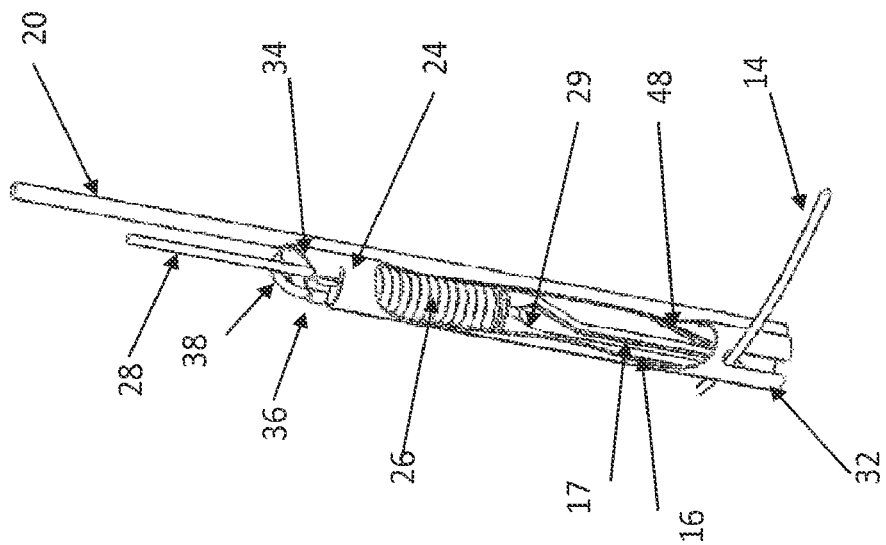
FIGS. 4-6 are perspective views of an anchor launching mechanism of the device of FIG. 1.
Figure 4:
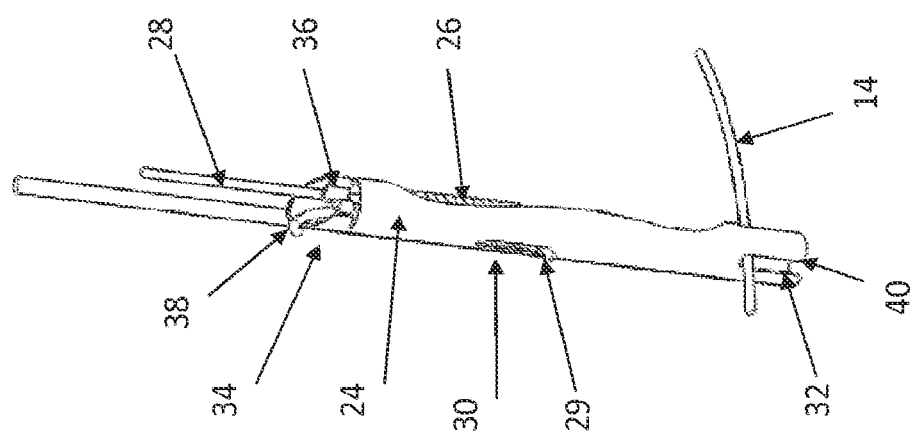
Figure 6:
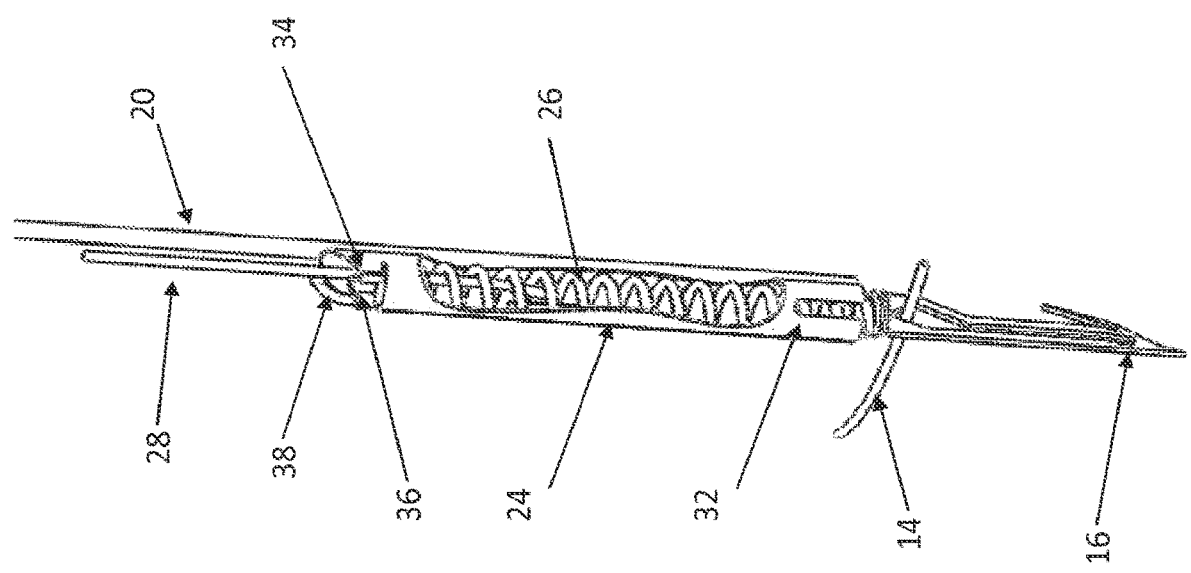

FIGS. 4-6 show details of anchor launching mechanism 22, which comprises a housing 24, typically cylindrical; an anchor launching biasing mechanism, such as coil spring 26 disposed within the housing; and a spring actuator wire 28, having a bent distal end 29, passing through elongated slot 17 and protruding through a window 30 of housing 24. Bent distal end 29 maintains spring 26 is a compressed configuration. Actuator wire 28 passes longitudinally/coaxially through coil spring 26. Implant support arms 20 are respectively attached to housings 24, for example by welding. It should be noted that actuator wire 28 can be made of any appropriate material and is not limited to metal.

Housing 24 has an open end 32 and a spring retention end 34, which in some embodiments comprises a crimped portion 36 or other such spring retention mechanism, to provide a launching base for spring 26. In some embodiments, to prevent spring 26 from being ejected from (falling out of) housing 24, spring has a hooked proximal end 38 adapted to hook at retention end 34 of the housing. As can be seen, loop 14 is threaded through each elongated slot 17 of tissue anchors 16. As best seen in FIG. 4, in some embodiments, housing 24 has a pair of elongated recesses 40 at open end 32 whereby loop 14 can pass. FIGS. 4 and 5 show anchors 16 in a pre-launch state where spring 26 is compressed, and FIG. 6 shows the anchors in a launched state with the spring in its normally expanded configuration.

As shown, tissue anchors 16 are typically spaced apart all along loop 14 and loop 14 is threaded through elongated slot 17, allowing the tissue anchor to move (be launched), typically more or less perpendicular (although in some embodiments at an angle) with respect to the loop. It should be noted that loop 14 can be made of any appropriate material and is not limited to metal. Note that while eight anchors are depicted in all the illustrated embodiments, the number of anchors can be varied. Preferably at least six anchors are used.

Figure 7A:
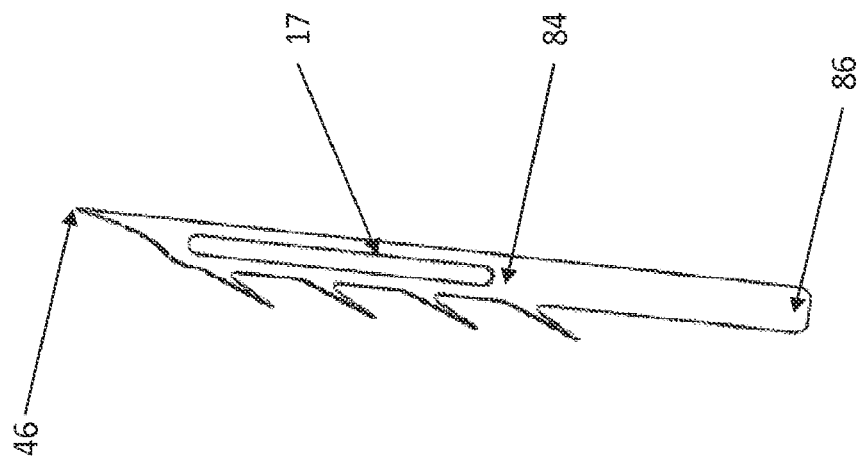
FIGS. 7 and 7a are perspective views of anchors of the present device.
Figure 7:
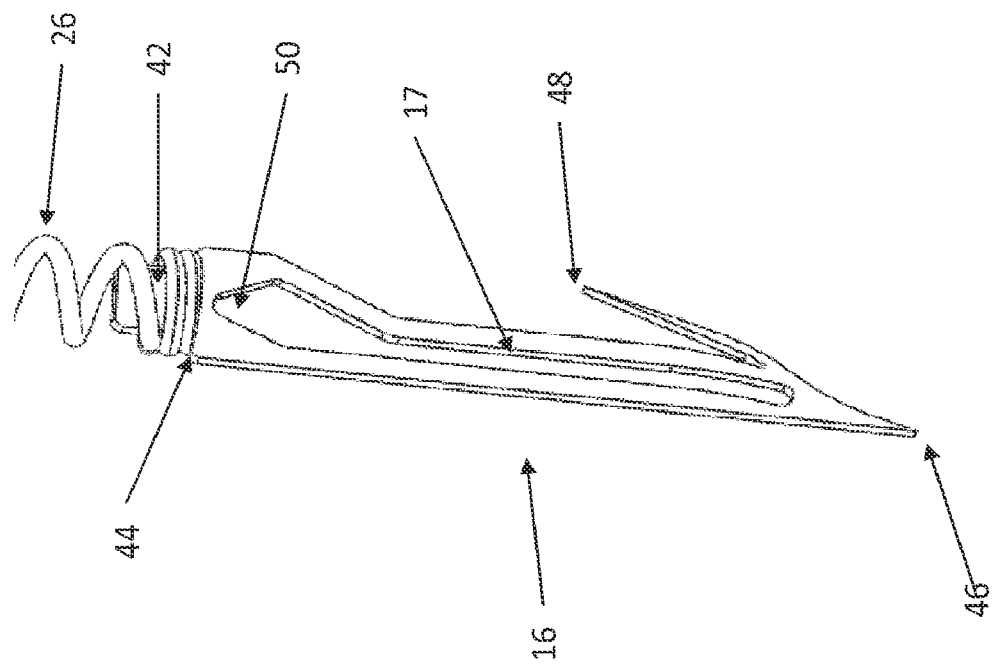

With reference to FIG. 7, in some embodiments, each anchor 16 has a proximal portion 42 including a spring interfacing portion exemplified by a pair of flat shoulders 44. Anchors 16 also have a pointy front end 46, typically with one or more barbs 48. After an anchor is implanted in the forward direction, the barbs 48 resist extraction of the anchor 16 in a backwards direction. In some embodiments, elongated slot 17 has a relatively large or bulbous open portion or eyelet 50 adjacent proximal portion 42, which can be useful to provide additional space for bent distal end 29 to pass through the elongated slot along with loop 14.

Figure 8:
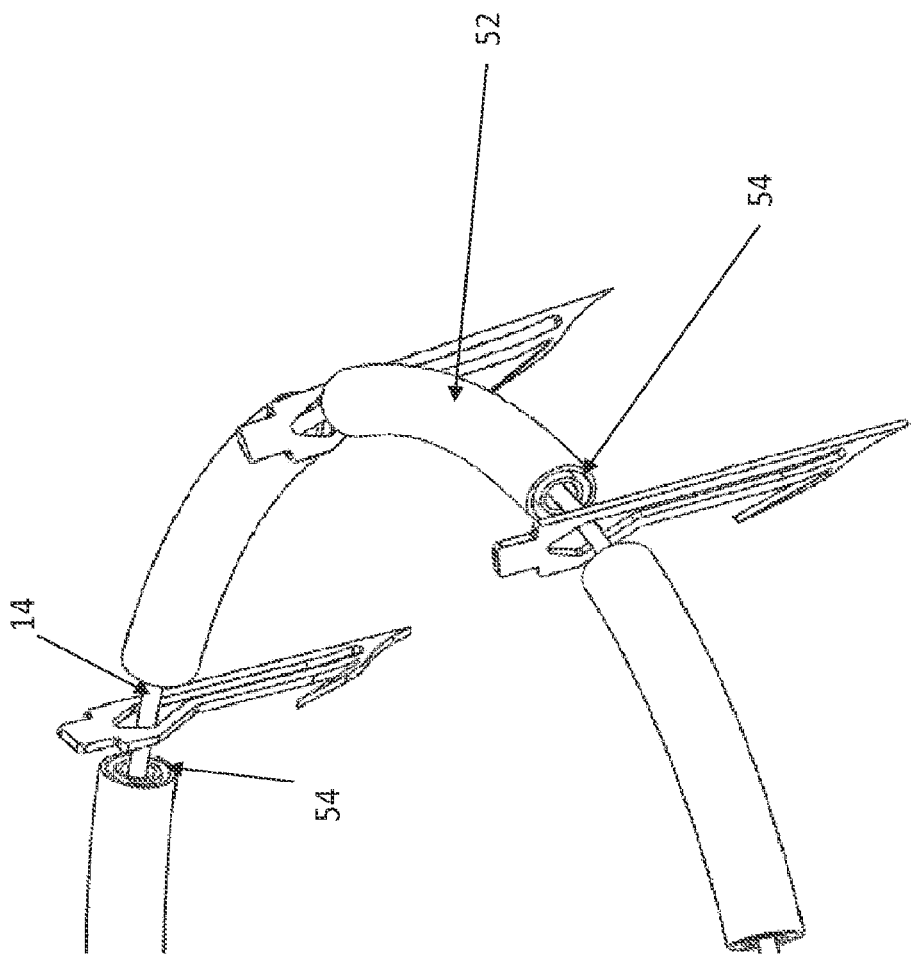
FIGS. 8-10 are perspective views of an another embodiment of the tissue engaging member.
Figure 9:
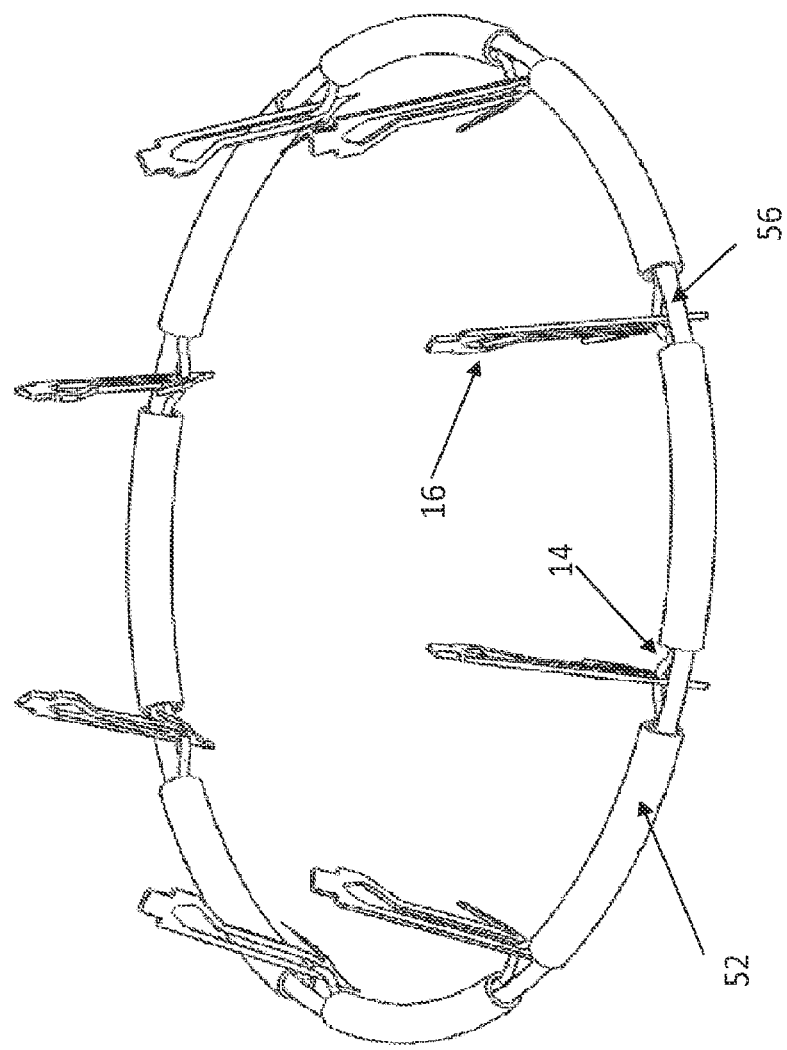
Figure 10:
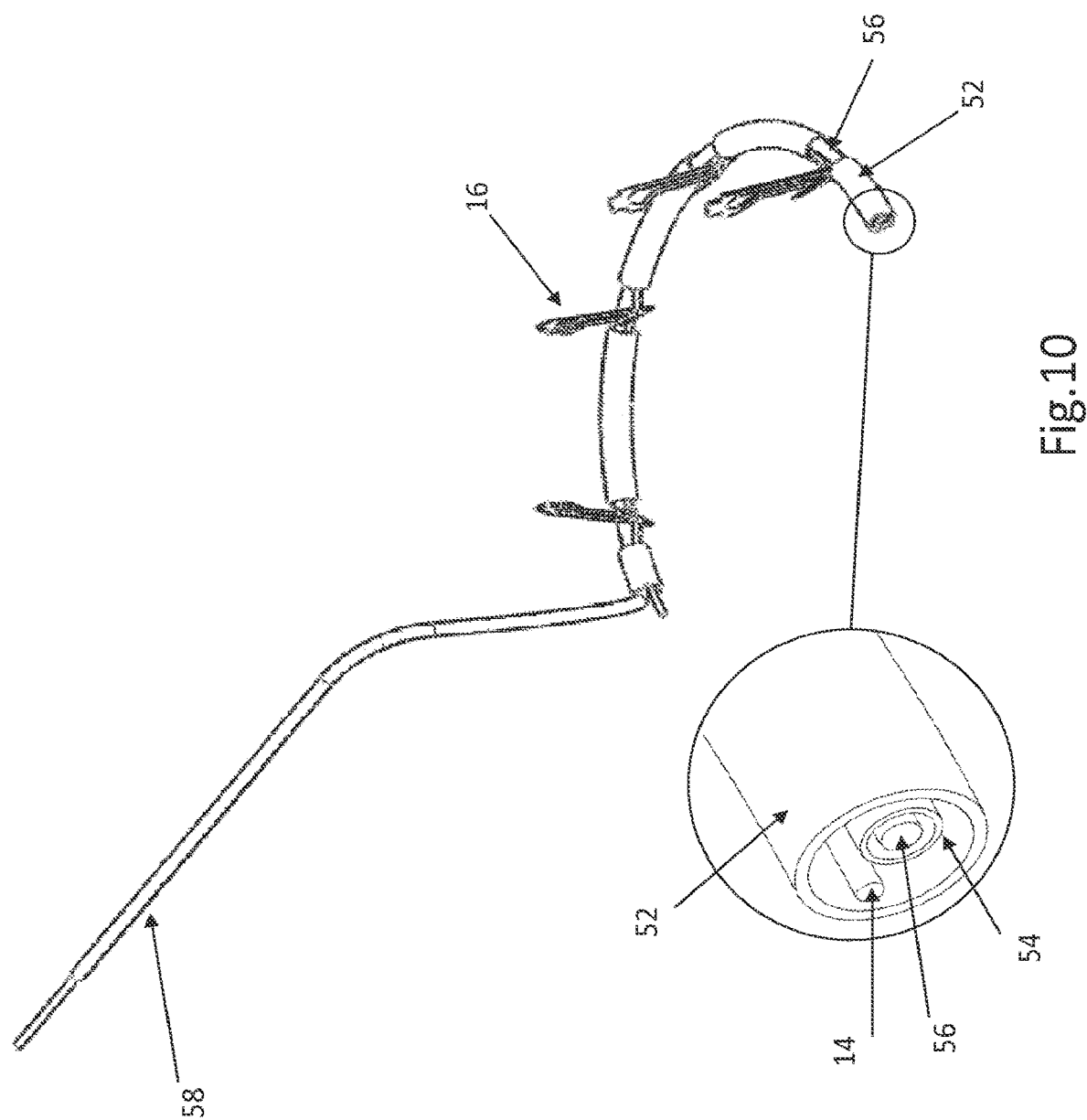

FIGS. 8-10 shows a modification of the implant wherein loop 14 has a plurality of tissue growth-promotion tubes 52 coaxially surrounding the loop between anchor positions. In some embodiments, tissue growth-promotion tubes 52 have respective tissue growth inhibiting liners or surfaces 54 (FIG. 10). Tissue growth-promotion tubes 52 are made of a material and/or substance adapted to promote and facilitate the growth of tissue thereon, for example an appropriate fabric or coating. If indeed in the form of liners, tissue growth inhibiting liners 54 are disposed tissue growth-promotion tubes 52, e.g. coaxially, and include tissue growth inhibiting material/substance.

FIGS. 9 and 10 additionally show another embodiment wherein there are two loops, the aforementioned loop 14 and a relatively sturdy auxiliary loop 56 to provide additional robustness to the implant if so desired. FIG. 10 shows a modification wherein auxiliary loop further includes a proximal portion 58 that can be used to position the implant 10, in addition to or in place of the above mentioned implant positioning device 18.

Operation: implant 10 is deployed to a position adjacent the bio-valve (e.g. Mitral valve M) via/through delivery catheter C (see FIGS. 11 and 12; and also FIGS. 1 and 2). When implant 10 is appropriately located, using support arms 20 and\or auxiliary loop 56 with its proximal portion 58, actuator wire 28 of each anchor launching mechanism 22 is retracted thereby withdrawing their bent distal ends 29 from respective windows 30 of housings 24. As a result, springs 26 are released from their compressed state to their expanded state thereby launching tissue anchors 16 into the bio-valve tissue. Typically, pointy end 46 of each anchor 16 enters the tissue, and barbs 48 help to prevent inadvertent detachment of the anchors.

FIG. 13 illustrates implant 10 connected to the tissue of mitral valve M of the heart after the launching of tissue anchors 16 into the tissue. Implant 10 is positioned on the top of the mitral valve M, as a result of being inserted into the heart in a manner such as shown in FIG. 1, and anchors 16 face generally downward. After the implantation natural tissue growth start to occur all around the parts of implant 10 that are within the tissue notably the anchors, and later on tissue growth will cover also parts of the implant at close proximity to the tissue surface. When tissue growth fills the anchors slot 17 they become mechanically locked within the tissue, and over time the entire implant 10 will get embedded in the valve annulus tissue. Since the implant is largely comprised of loop 14 which is made of non elastic substance, further annulus dilatation over time due to progression of the valve regurgitation disease is prevented.

With reference to FIG. 14, in some embodiments, the implant further comprises a cinching mechanism 60, for example wherein loop 14 is not in a closed loop configuration rather has generally adjacent free ends 62 and 64. The ring-like portion of loop 14 passes through elongated slots 17 of anchors 16 (and in suitable embodiments, through tissue growth-promotion tubes 52), as before. After sufficient tissue grows on implant 10, which typically takes one week to several months, depending on the tissue growth rate, the implant may be cinched via pulling on one or both of the free ends 62 and/or 64 to reduce the diameter of tissue engaging member 12, (however, in some implementations of the operation, cinching action is not required, and could be excluded from procedure). Free ends 62 and 64 may extend outside the patient's body or remain under the skin at the upper portion of the chest, much like pace maker leads. The tissue growth causes implant 10 to be embedded and integrated to the valve annulus. In addition, tissue growth within elongated slot 17 helps secure anchors 16 and prevents the implant from being dislodged from the valve annulus.

FIG. 14 further illustrates a D-shaped loop 14, in contrast to the circular or oval shaped loops illustrated in the aforementioned figures. D-shaped loop 14 is particularly suited for use with a human mitral heart valve. In this regard, it should be understood that loop 14 can be configured by choice or design to appropriately correspond to the particular bio-valve for which repair is required.

Figure 15:
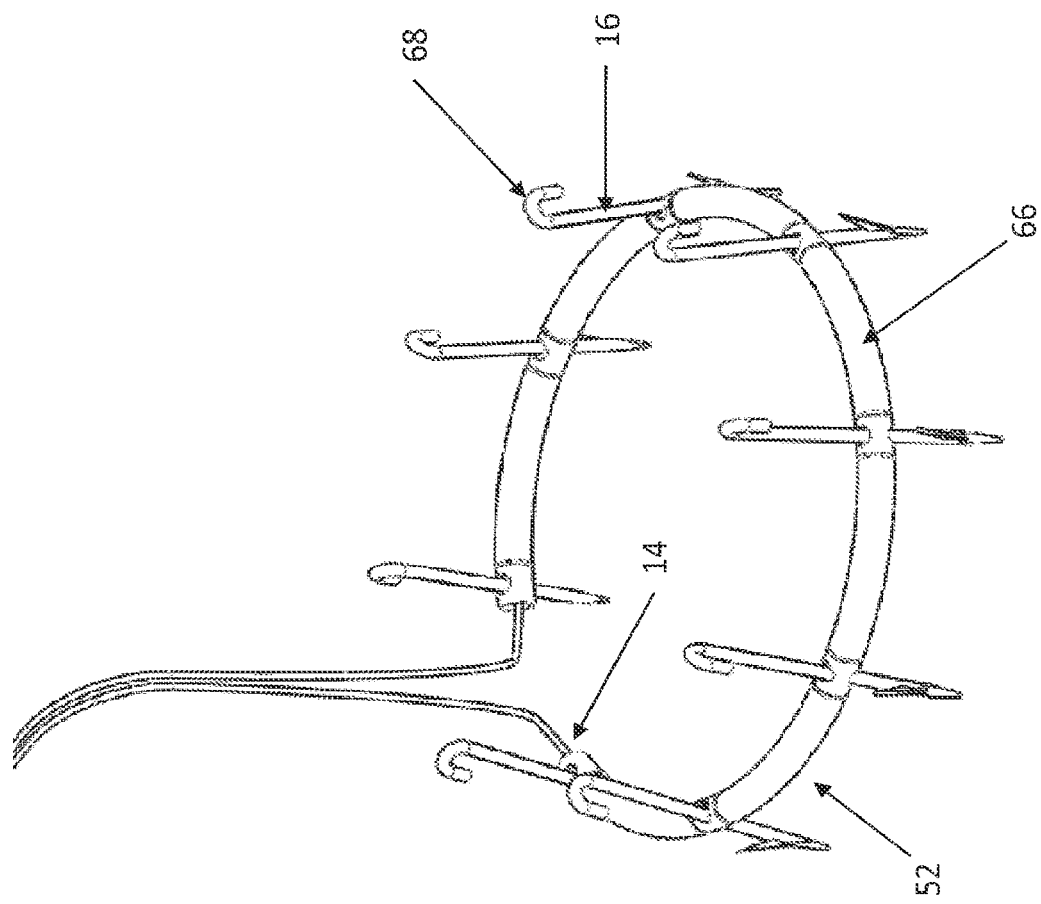

FIG. 15 shows another embodiment wherein instead of anchors 16 engaging loop 14 via elongated slot 17, the anchors pass thru a coaxial tube 66 coaxially surrounding the loop—the tube could be, for example a tissue growth promotion tube such as tissue growth-promotion tubes 52. Retention of anchors 16 with coaxial tube 66 is aided by a retention hook 68 at the proximal end of the anchors.

FIGS. 16 and 17 depict an embodiment where anchor 16 has a cylindrical shape, similar to housing 24 and no such housing is required. In this case spring 26 is held in compression between end 34 of cylindrical anchor 16 and a spring launching base, exemplified by a launching base ring 70, attached to implant support arms 20. End 34 now provides the function of the aforementioned flat shoulders 44; and launching base ring provides the function of the aforementioned crimped portion 36. When actuator wire 28 is retracted, its bent distal end 29 (here, illustrated in the form of a half-loop) is retracted from window 30 thereby releasing cylindrical anchor 16 so that spring 26 expands to launch the anchor.

Figure 19:
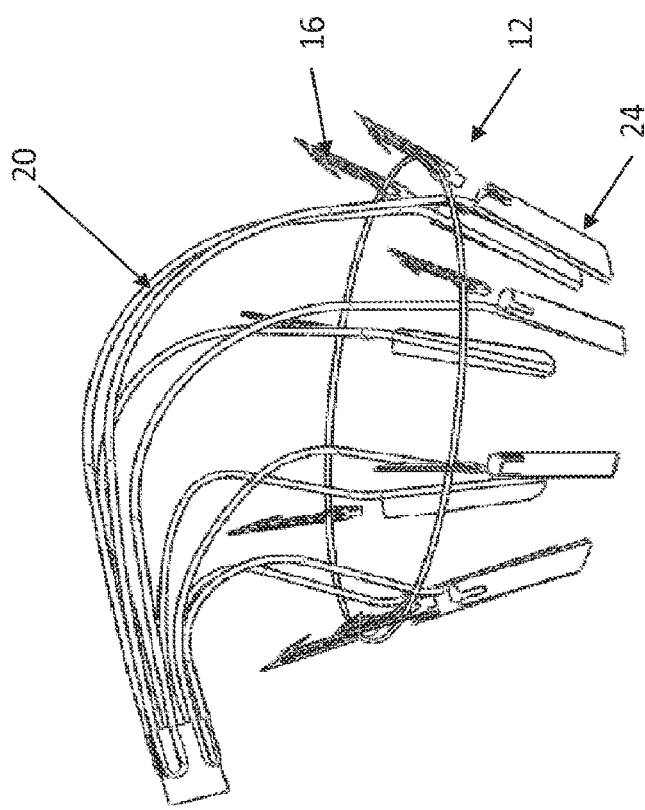
FIGS. 18 and 19 are perspective views of embodiments of anchor launching mechanisms.
Figure 18:
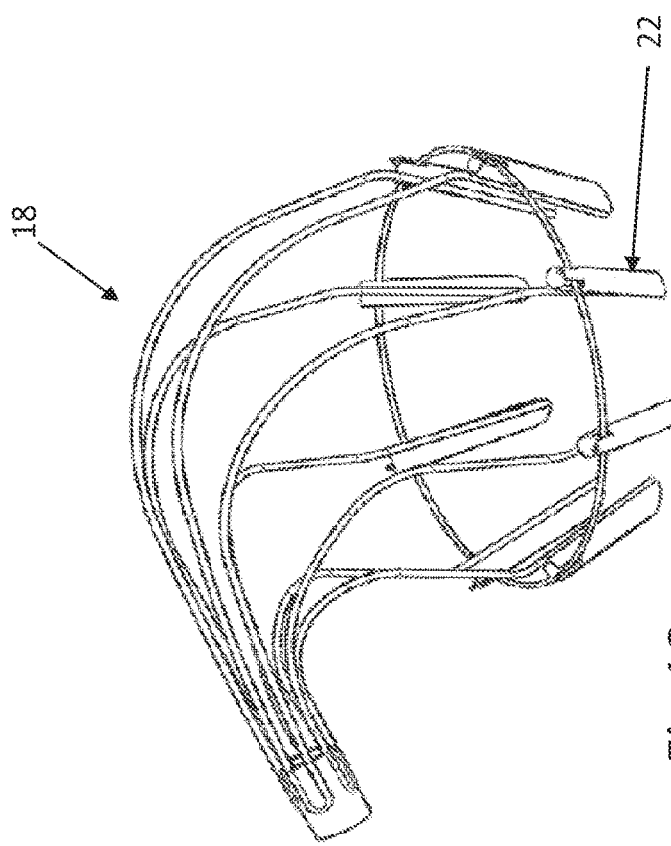

FIGS. 18 and 19 shows implant positioning device 18 configured, mutatis mutandis, wherein anchor launching mechanism 22 is adapted to launch anchors 16 into the tissue in a generally upward direction (i.e. from the ventricle side to the atrium side). This embodiment is particularly useful in the case where the tissue engaging member 12 serves as a support to prevent dislodgement of a valve prosthesis that can be expanded into it right after the tissue engaging member 12 has been deployed.

Figure 20:
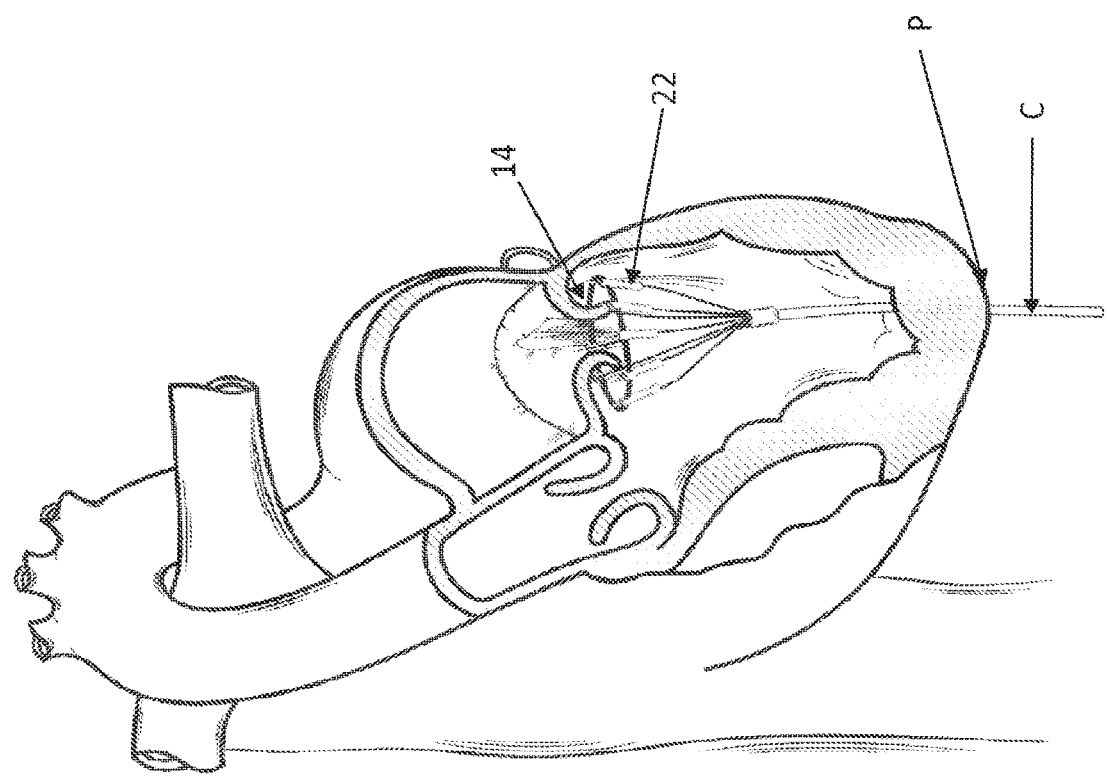
FIGS. 20-22 are front partially cut-away views of a heart with the implant affixed to a mitral valve from below the valve.
Figure 21:
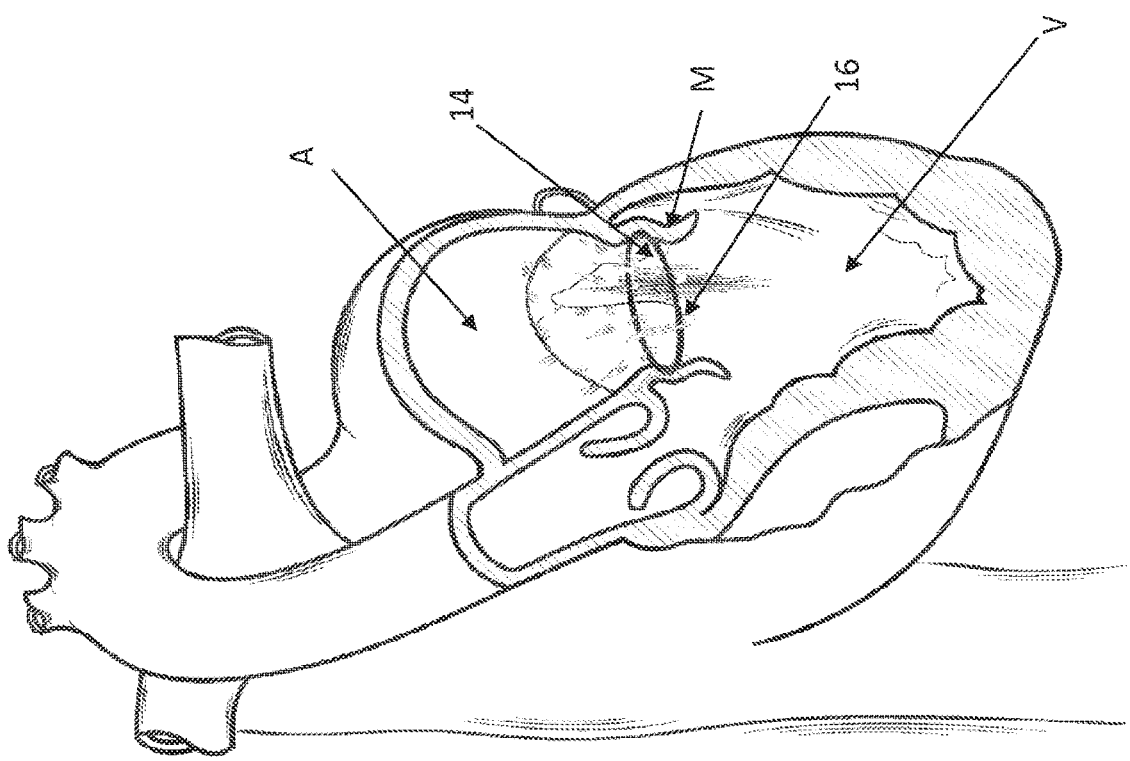
Figure 22:
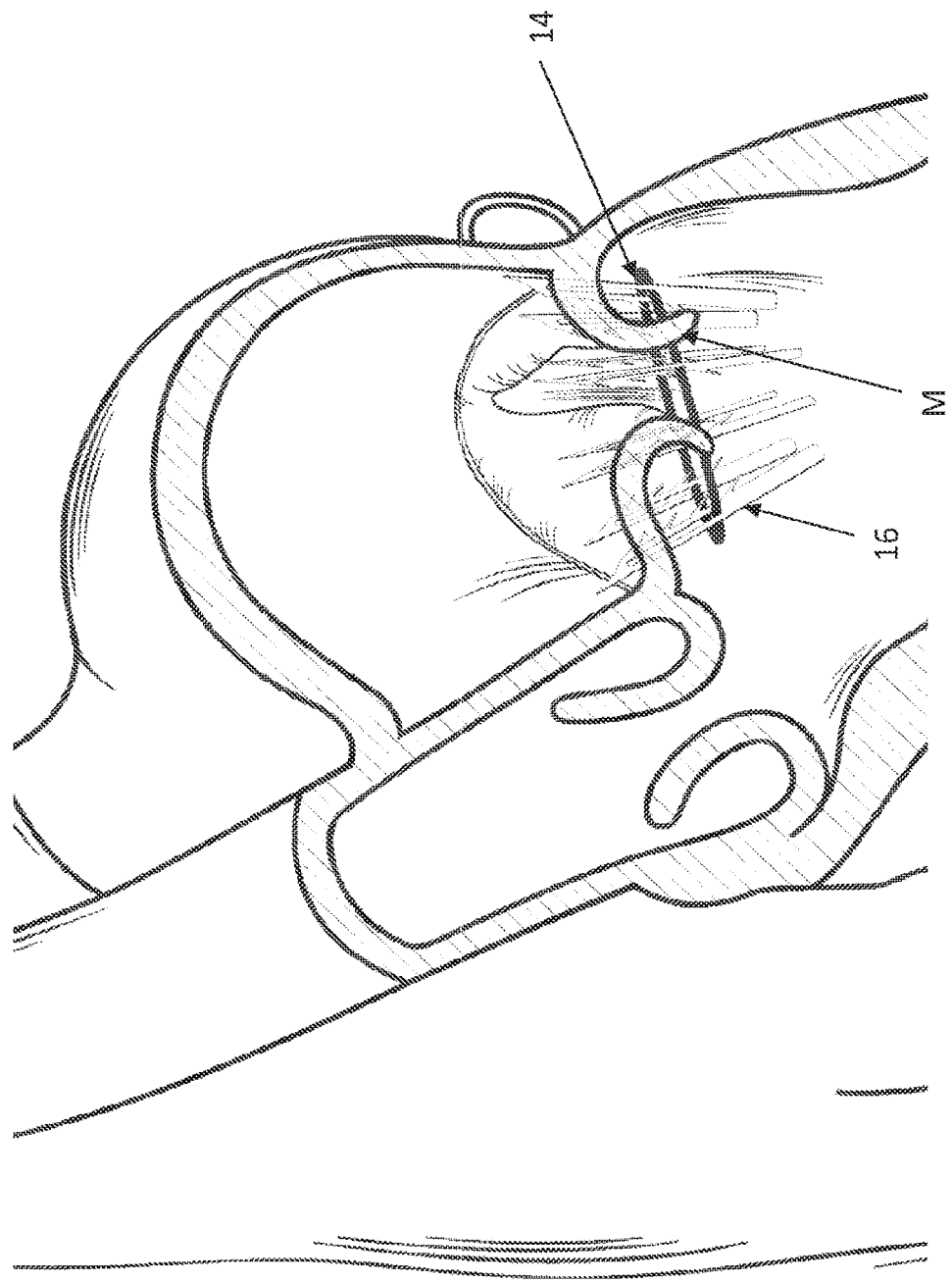

FIGS. 20-24 illustrate embodiments adapted for situations where launching anchors 16 upwardly may also be used in cases where access to the insufficient valve is from below, for example via the Apex (see FIG. 20), is preferable rather than from above. FIGS. 20 and 22 show loop 14 disposed under the Mitral valve leaflets and FIG. 21 shows loop 14 disposed onto the Mitral valve leaflets M as the anchors 16 penetrates through the leaflets pointing from the ventricle side to the atrium side.

Figure 23:
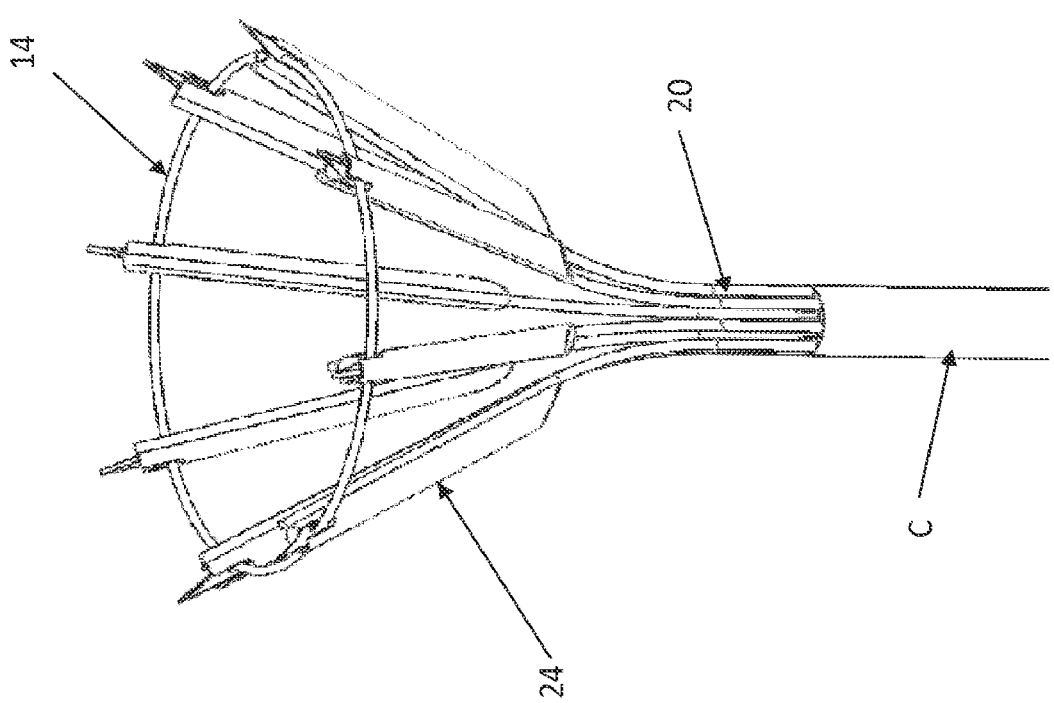
Figure 24:
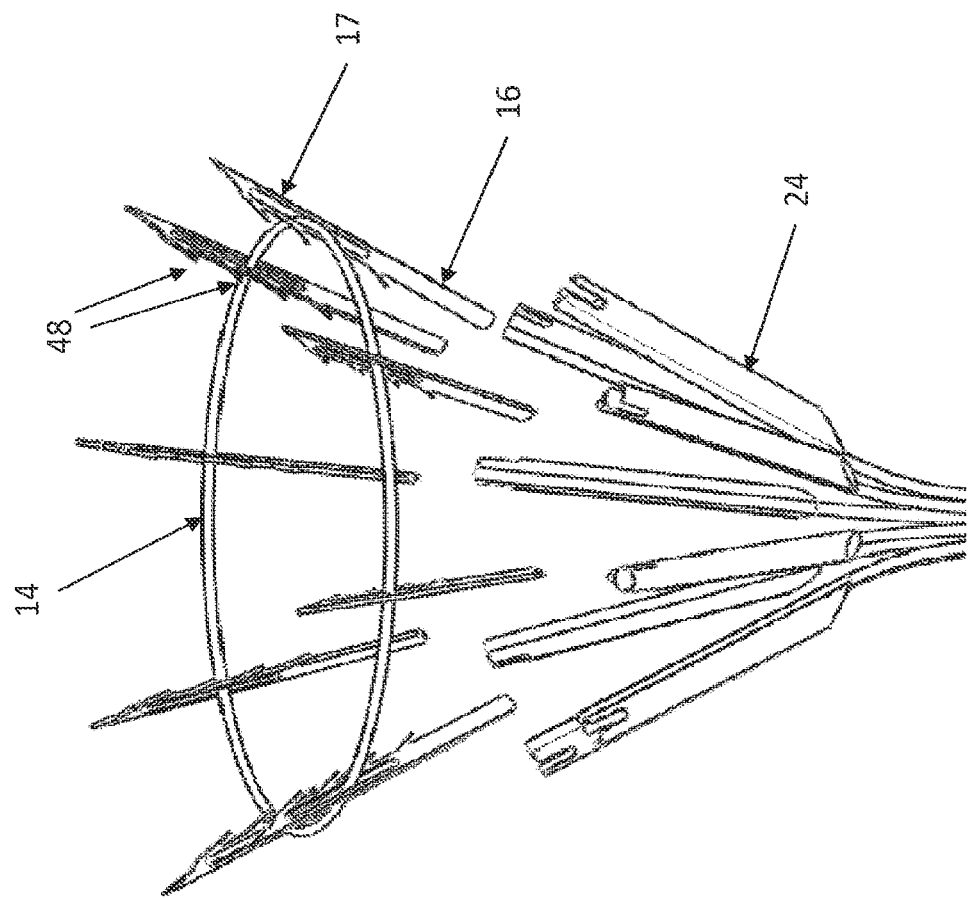

FIGS. 23 and 24 show the pre-launch and launch situations for upward launching of anchors 16. FIG. 23 further illustrates that catheter C can be used to help orient the angle of housings 24, and thus the launch angle of anchors 16. If the distance between catheter C and loop 14 is relatively small, anchors 16 tends to be positioned and launched at a greater angle (relative to being launched perpendicular to loop 14, as was shown in FIGS. 2 and 3, for example). Adjustment of the launch angle. i.e. pivoting of anchors angle, is made possible by the shape of the support arms 20 to which the housing 24 is attached. FIG. 24 also illustrates another modification wherein anchors 16 comprise multiple barbs 48 and wherein elongated slot 17 extends about half-way within the length of the anchors.

FIGS. 25-27 and 27a illustrate particular embodiments wherein anchor launching mechanism 22 is adapted to be used with tissue anchors 16 that are launched in a generally upward direction; and can be actuated by a direct pull, or by a mechanism removed from the valve area. Anchor launching mechanism 22 comprises actuation wire 28 and housing 24, however the mechanism does not include spring 26 disposed in the housing. Regardless, for rapid actuation purposes (anchor launch), anchor launch mechanism 22 may further include an external launch actuator device, typically including a spring (not shown), for example, at the proximal end of catheter C, to pull on actuation wire 28. When the catheter approaches from the inflow side of the valve, and routes the anchors so that they are below the valve with the tip directed from the ventricle side to the atrium side, this configuration and approach to the valve permits pull wires to be used.

Figure 26:
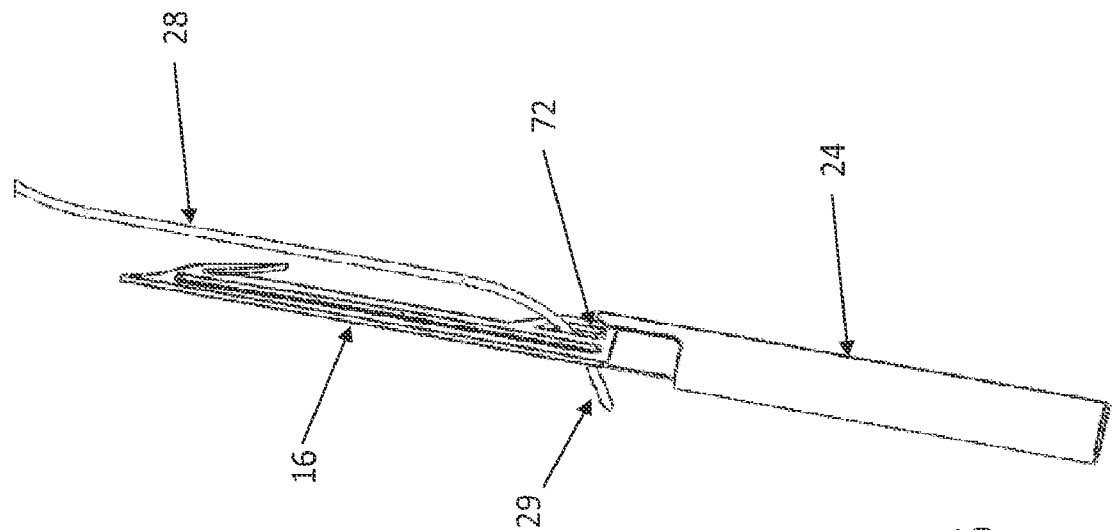
Figure 25:
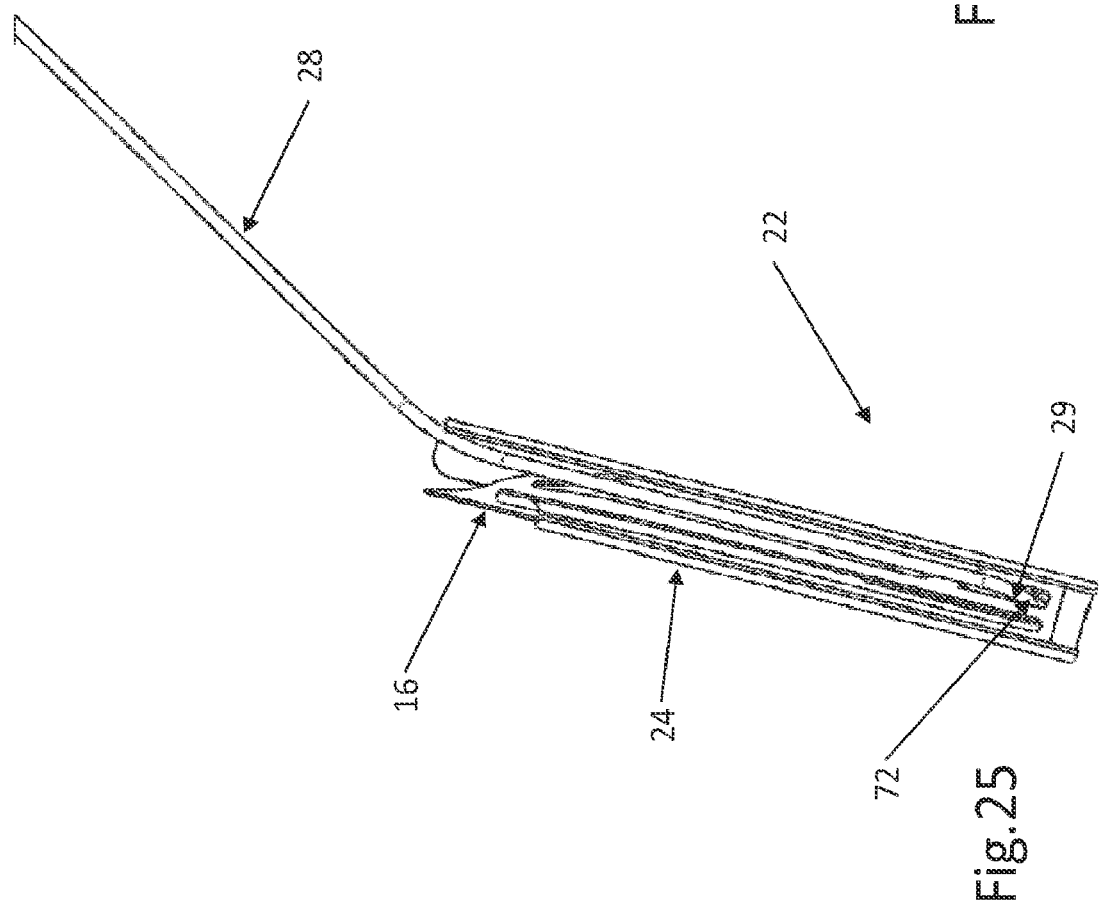

For the purposes of these embodiments, anchor 16 may be modified to further comprise an actuation wire eyelet 72 where-through actuation wire 28. Distal end 29 of actuation wire 28 is threaded through eyelet 72 and typically has a hook-like configuration while disposed within housing 24 (FIGS. 25 and 27). Pulling on actuator wire 28 proximal end to pull (launch) anchor 16 as a result of pulling at eyelet 72 (FIG. 26). In such embodiments, housing 24 need not include a window such as window 30, nor does not need a crimped portion 36 or other such spring retention mechanism, as there is no spring in the housing. FIGS. 27 and 27a illustrates a modification wherein instead of eyelet 72; each anchor 16 has a actuator-wire distal-end receiving portion such as recess 74, which operates to launch anchors 16 in the same fashion as noted above.

Figure 28:
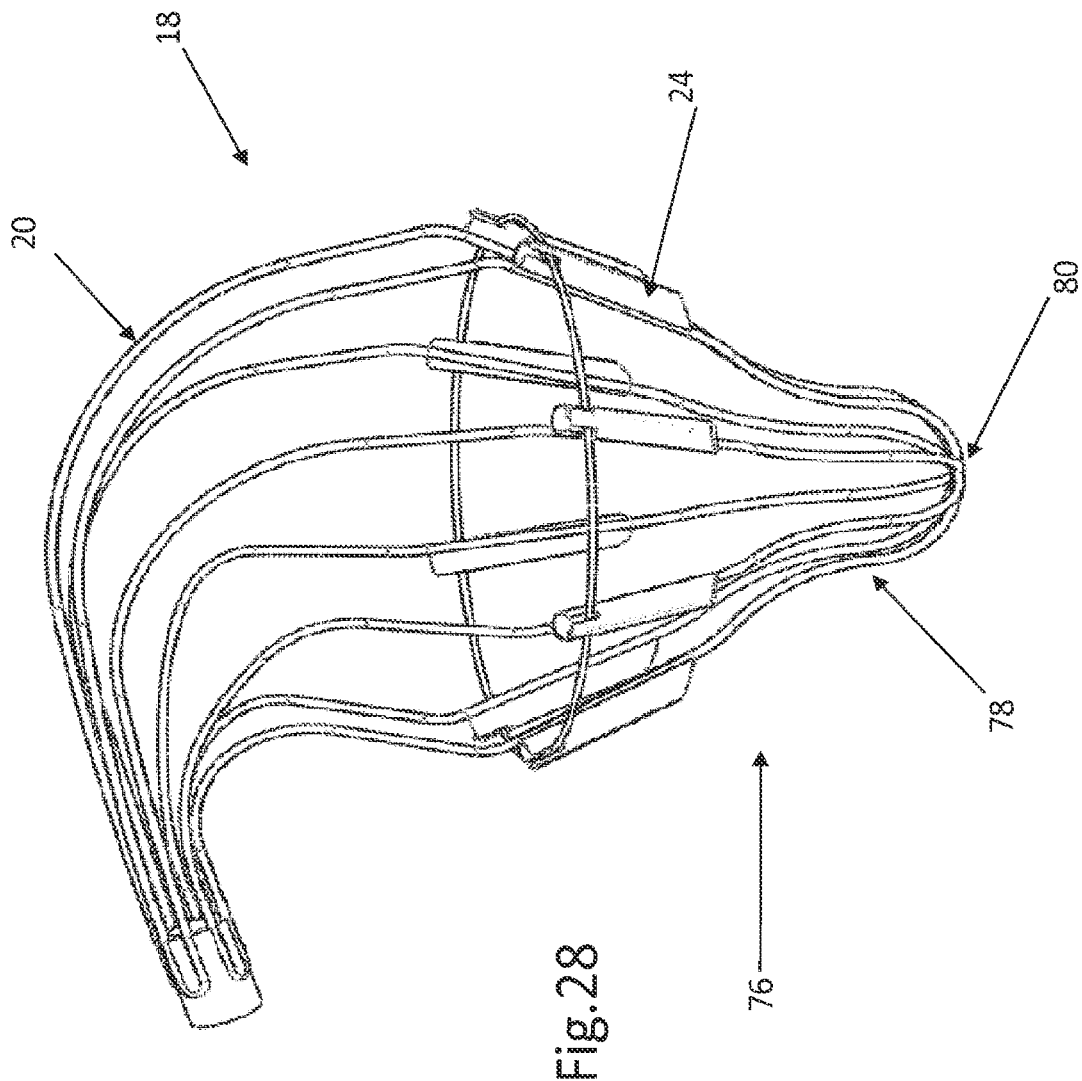
FIGS. 28-30 are perspective views of implant deployment mechanisms.
Figure 29:
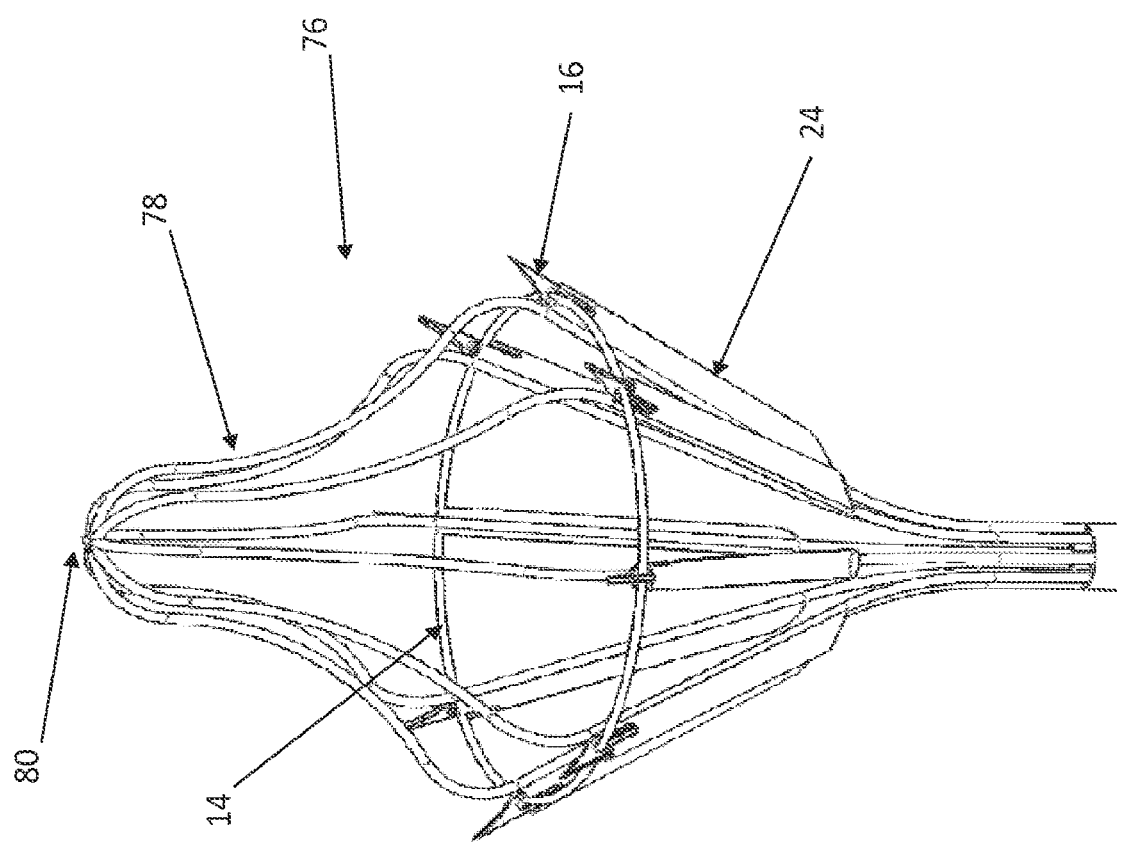
Figure 30:
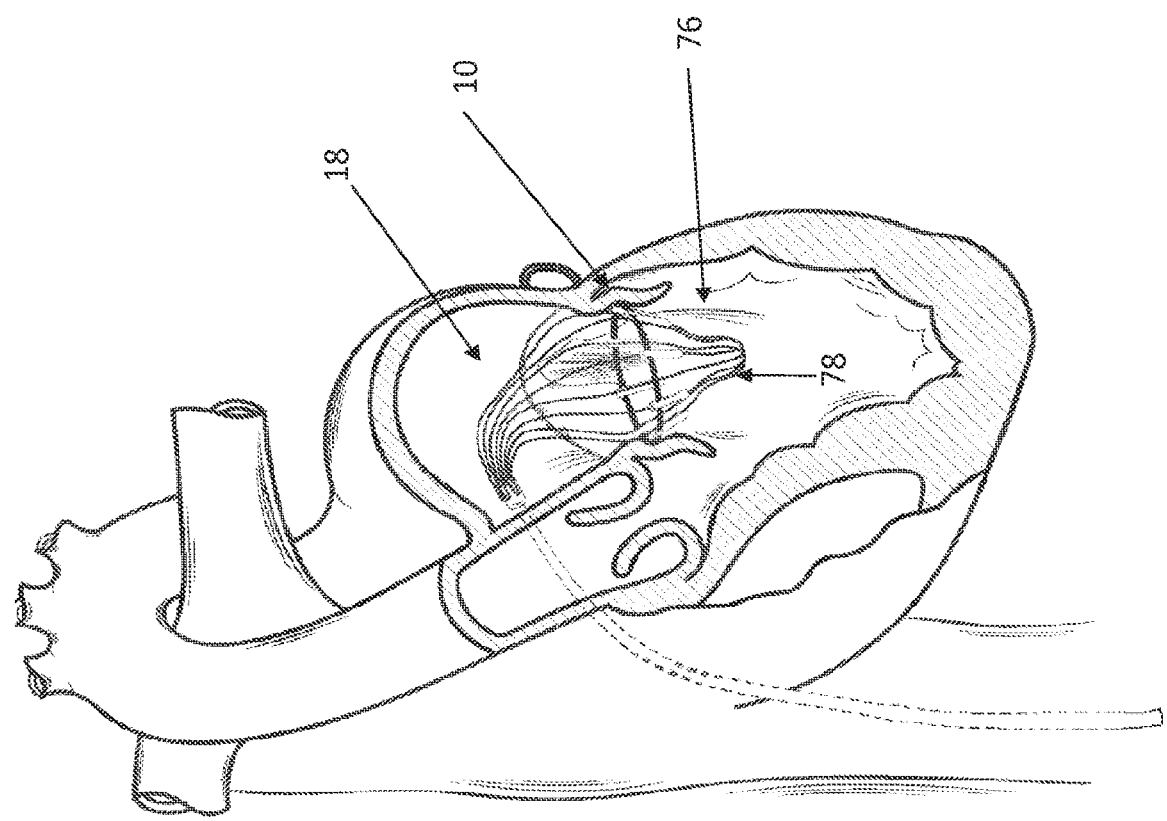

FIGS. 28-30 show embodiments, wherein implant 10 further comprises a loop-arrangement/anchor-orientation mechanism 76 useful for arranging the position and/or shape of loop 14 and/or for orienting the angle of housings 24, and thereby orienting the launch angle of tissue anchors 16. Anchor orientation mechanism 76 includes a plurality of curved arrangement leads 78 respectively attached to at least some of housings 24, for example by welding. Leads 78 may be an extension of implant support arms 20 and may be arranged to cross at a singular intersection point 80. Leads 78 are attached (e.g. by welding) to housing 24. Thus, leads 78 of orientate mechanism 76 are movable to arrange loop 14 in a desired location and depending on the shape of the leads, the angle of housings 24, and thus anchors 16, can be determined.

Regarding the launch angle of anchors 16, in some embodiments, leads 78 can be attached "ad hoc" prior to insertion into a patient, whereby, depending on the attachment location, arrangement leads 78 also be used to orient anchors 16 i.e. control the angle at which the anchors enter the tissue (i.e. changing the length or shape of one or more leads 78 will thus change the angle of the anchors, e.g. shortening the that length will cause the anchors to point outward, whereas increasing that length will bring intersection point 80 farther from loop 14 and thus angle the anchors more parallel to each other (less outward). In such case, leads 78 will not be welded to housings 24, rather there will be included an "ad hoc" connection or fastening arrangement (not shown), whereby the leads and housings are connected at more than one location along the leads.

Arrangement/orientation mechanism 76 can be useful for arranging the shape of loop 14 as well as positioning the loop and orienting the anchor angle. In alternative embodiments, loop-arrangement/anchor-orientation mechanism 76 either has a predetermined shape, such as a nipple shape (FIGS. 29 and 30) or is adapted to allow its shape to be changed; i.e. leads 78 can be bent.

FIGS. 31-34 show embodiments wherein loop arrangement and/or implant positioning device 18 comprises an inflatable balloon 82. The figures show exemplary balloons 82 useful for a) making sure support arms 20 are fully expanded before deploying implant 10, b) make sure that loop 14 is concentric with the valve annulus prior to implantation, and c) facilitating an interference step or backing against which to press to be used for pressing implant positioning device 18 and implant 10 onto the valve annulus before implantation as illustrated in FIG. 34. FIG. 31 illustrates an oval balloon 82; FIGS. 32-34 illustrate a droplet-shaped or bulbous balloon 82.

As seen in FIG. 34, as well as being useful to orient loop 14 relative to the valve annulus, the balloon can be used to secure the implant positioning device 18 and implant 10 in place during launching of anchors 16. FIGS. 32 and 33 also illustrate that balloon 82 can be positioned proximally or distally with respect to loop 14 and implant positioning device 18. Since the balloon can be positioned inside the ventricle and be inflated to a diameter bigger than the diameter of biological valve annulus, it can serve as a backing against which to press positioning device 18 and implant 10 onto the valve annulus before implantation. This will ensure good contact between each of the anchor launching mechanisms 22 and the valve annulus and will create optimal penetration conditions of anchor 16 into the tissue upon launching. Furthermore, the launch angle of anchors 16 (i.e. insertion into the tissue) can be controlled by inflating/deflating balloon 82, with consideration to the size of the biological valve.

Figure 35:
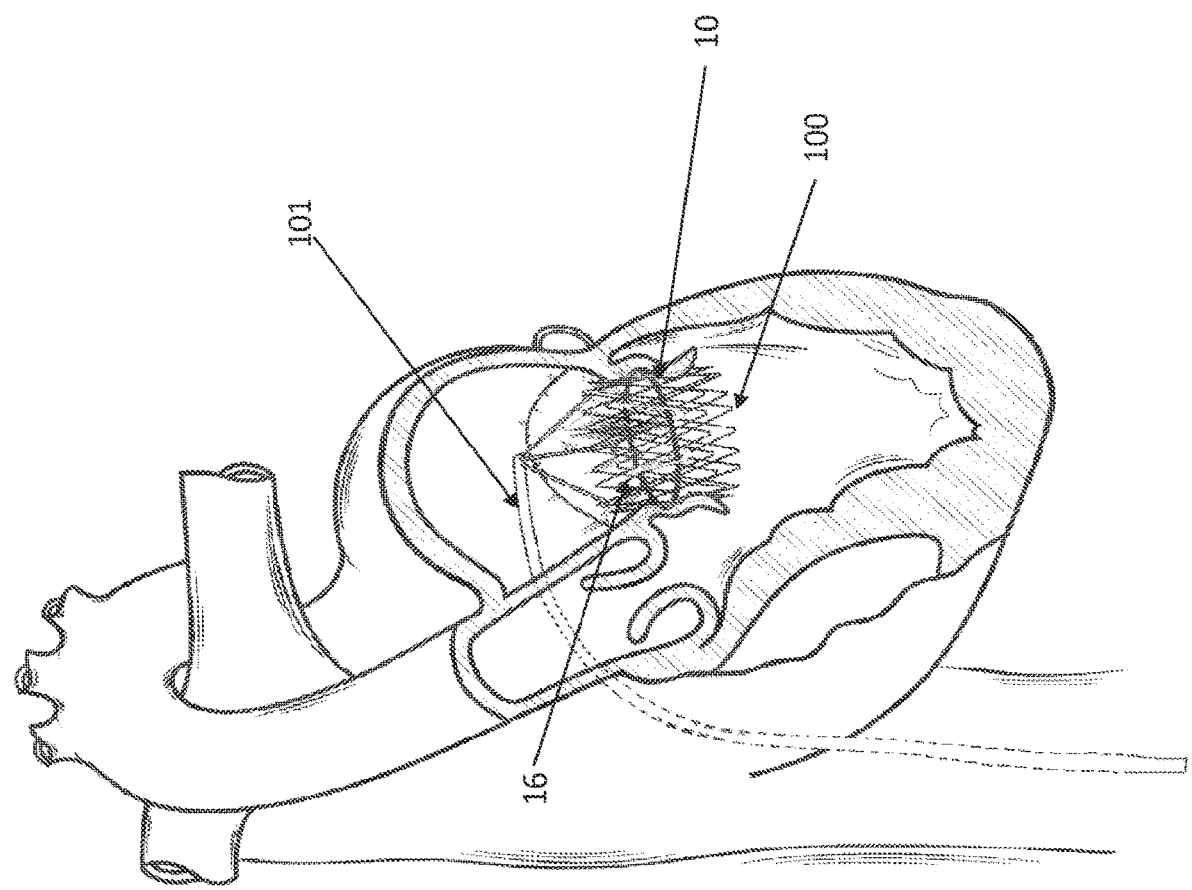
Figure 37:
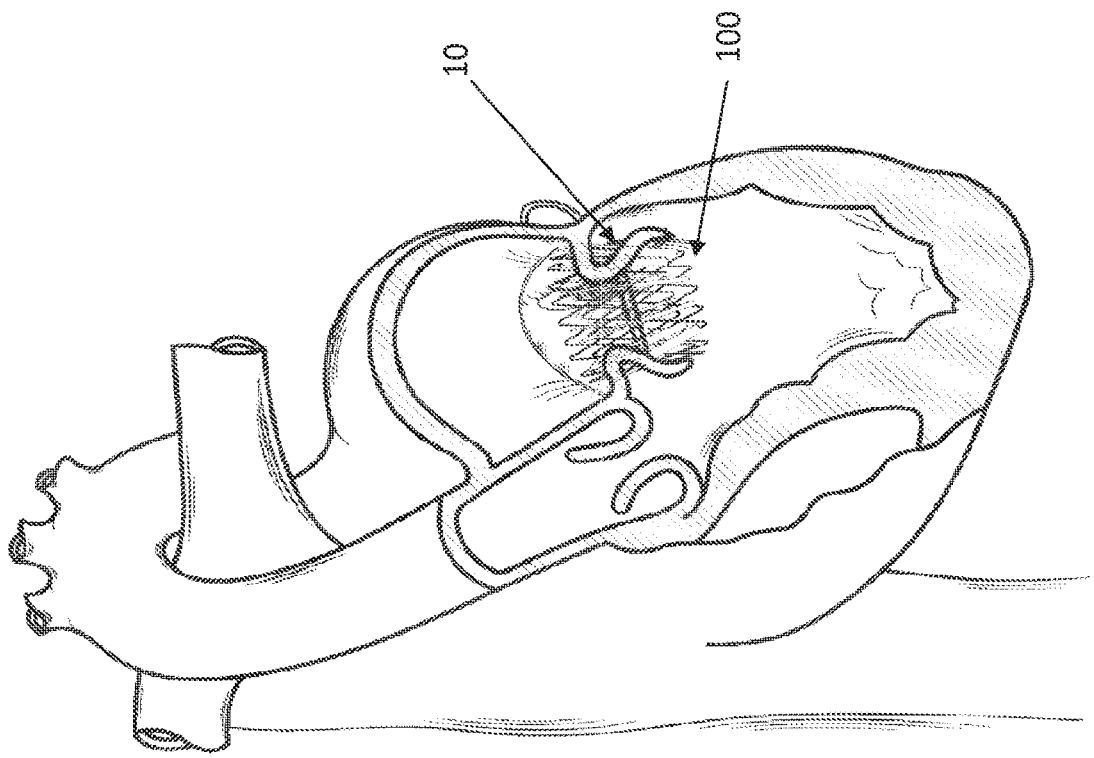
Figure 36:
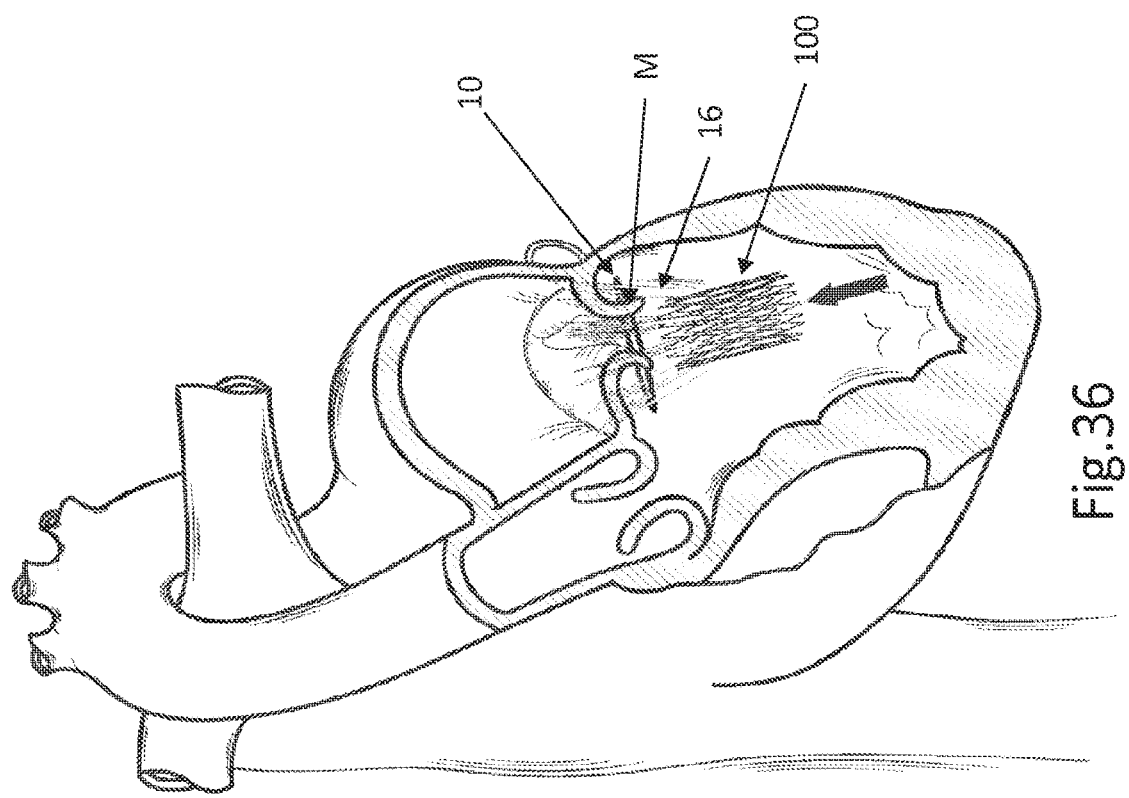

FIGS. 35-37 illustrate how a device 100 (e.g., a replacement valve) can be fixed to a native valve annulus or leaflets like the mitral valve M or tricuspid valve. In this embodiment, implant 10 is first implanted and secured with anchors 16 that penetrate the valve leaflets pointing from the ventricle V side toward the atrium A side (hereinafter upwards) as in FIG. 21 and/or FIG. 22. Then, when device 100 is expanded into implant 10, the friction between anchors 16 and the device 100 secures device 100 in place. Since anchors 16 are directed generally upward, the high pressure in ventricle V helps to further enhance the anchoring of implant 10 to the valve leaflets.

Device 100 in the illustrating figures represents any suitable commercial expandable heart valve prosthesis that can be tracked in a collapsed configuration through the vascular system and delivered to the heart. It can be a self expanding prosthesis or a balloon expanding prosthesis or any other type of expanding heart valve prosthesis. FIG. 35 further illustrates an exemplary delivery system 101 that can deliver device 100 to the heart.

FIGS. 36 and 37 illustrate how implant 10 can be associated with device 100 for fixing the device to a mitral valve M (or tricuspid valve) leaflets. In this embodiment, implant 10 and device 100 are implanted via the heart's apex P, preferably, in a minimally invasive surgery as illustrated in FIG. 20. As in FIG. 22, implant 10 is first located at the proper location with respect to the bio-valve (mitral in this case) and then secured with anchors 16 facing upward, in accordance with any appropriate embodiment as described herein. After implant 10 is attached to the valve leaflets, device 100 is advanced, as shown in FIG. 36, through a delivery catheter (not shown), and expanded into implant 10 as seen in FIG. 37. Since anchors 16 are directed generally upward, the high pressure in the ventricle V helps to further enhance the anchoring of the implant 10 and device 100 to the valve leaflets. However, for the purpose of this embodiment, wherein implant 10 is configured to be particularly suited to securing a device in place such as device 100, each anchor 16 has a relatively shorter slot 17, typically extending only about half-way along the longitudinal dimension of each anchor, from about halfway along the anchor to relatively close to the anchors' pointy front end 46.

With reference to FIGS. 38 and 39, when device 100 is disposed in the appropriate heart (or other biological) valve and expanded, the contact and sliding motion between the device and anchor 16 changes the angle of the anchors from typically approximately 45 degrees (FIG. 38), although, depending on the angle of support arms 20, to an angle wherein the anchors are more parallel to each other, typically substantially parallel. The movement of anchors 16 is illustrated by arc A-B in FIG. 38. In other words, anchors 16 pivots at the end of slot 17, as in FIG. 7a which is generally at mid-point 84 of the anchors. This angle change provides increased friction between anchors 16 and device 100 thereby securing the device in place.

To further explain, device 100 is expanded in the bio-valve until the device presses on a non-slotted portion 86 of anchors 16. As a result of pressing on non-slotted portion 86, that portion is forced outward, and thus the tip of the anchors 46 is moved inward, as the anchors pivot around loop 14. Since anchor tips 46 are locked within the tissue of the valve leaflet, the inward motion of the tips pulls the leaflets closer to device 100 and presses the leaflets against the device, thereby enhancing the sealing and prevent blood flow between the native valve leaflet and the device. It should be understood that device 100 is appropriately sized for the above-described positioning.

Figure 40:
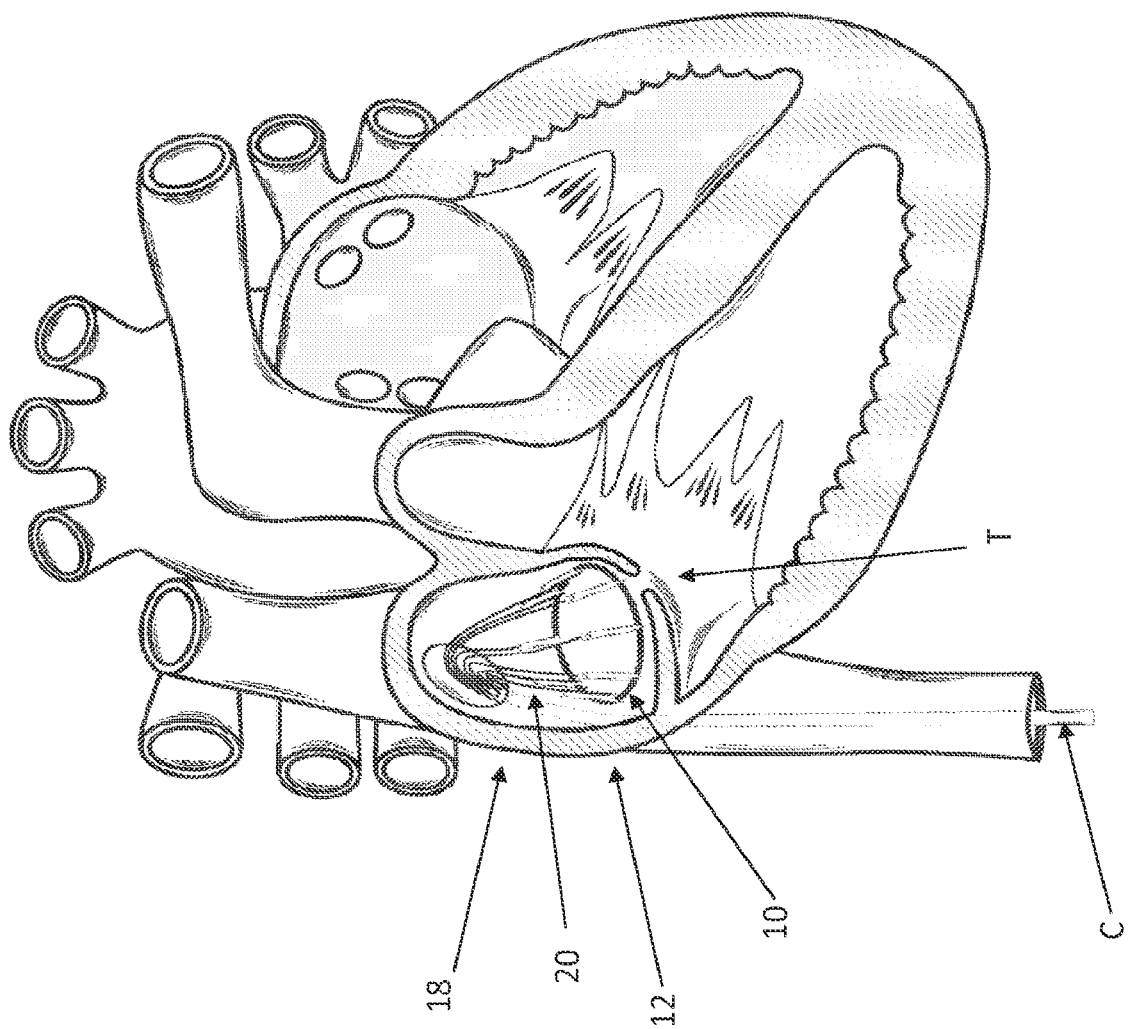
FIG. 40 is a perspective partially cut-away view of the heart with the implant deployed for use on a tricuspid valve.

FIG. 40 illustrates deployment of implant 10 in the tricuspid heart valve T and it should be understood that all the features and functions of the implant and delivery system as illustrated in FIGS. 1 to 39 are applicable to the tricuspid valve.

Figure 41:
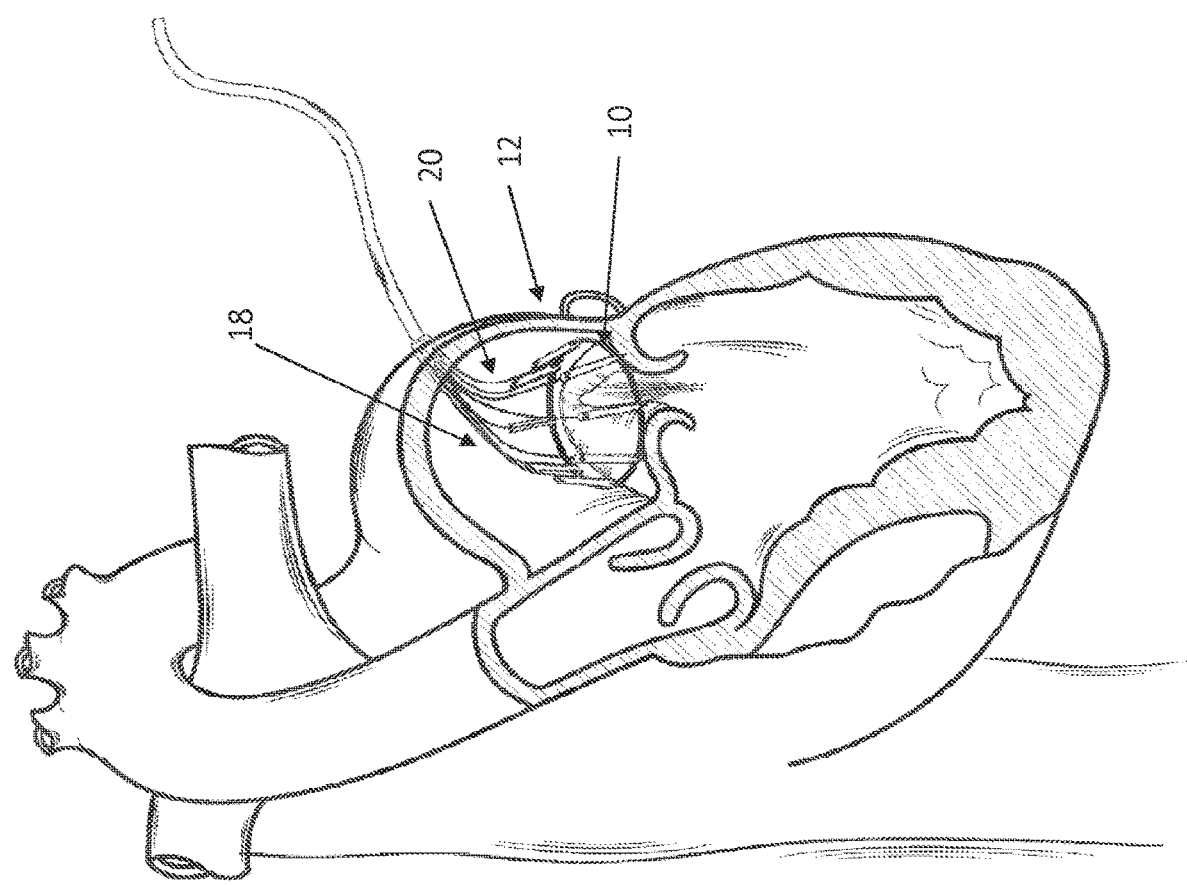
FIG. 41 is a perspective partially cut-away view of the heart with the implant deployed via the left atrium wall.

FIG. 41 illustrates deployment of implant 10 through the left atrium wall rather than tracking in through the vascular system, or deploying the implant through the apex of the heart. Again, it should be understood that all the features and functions of the implant and delivery system illustrated in FIGS. 1 to 39 are applicable to deployment through the atrium wall.

Figure 42:
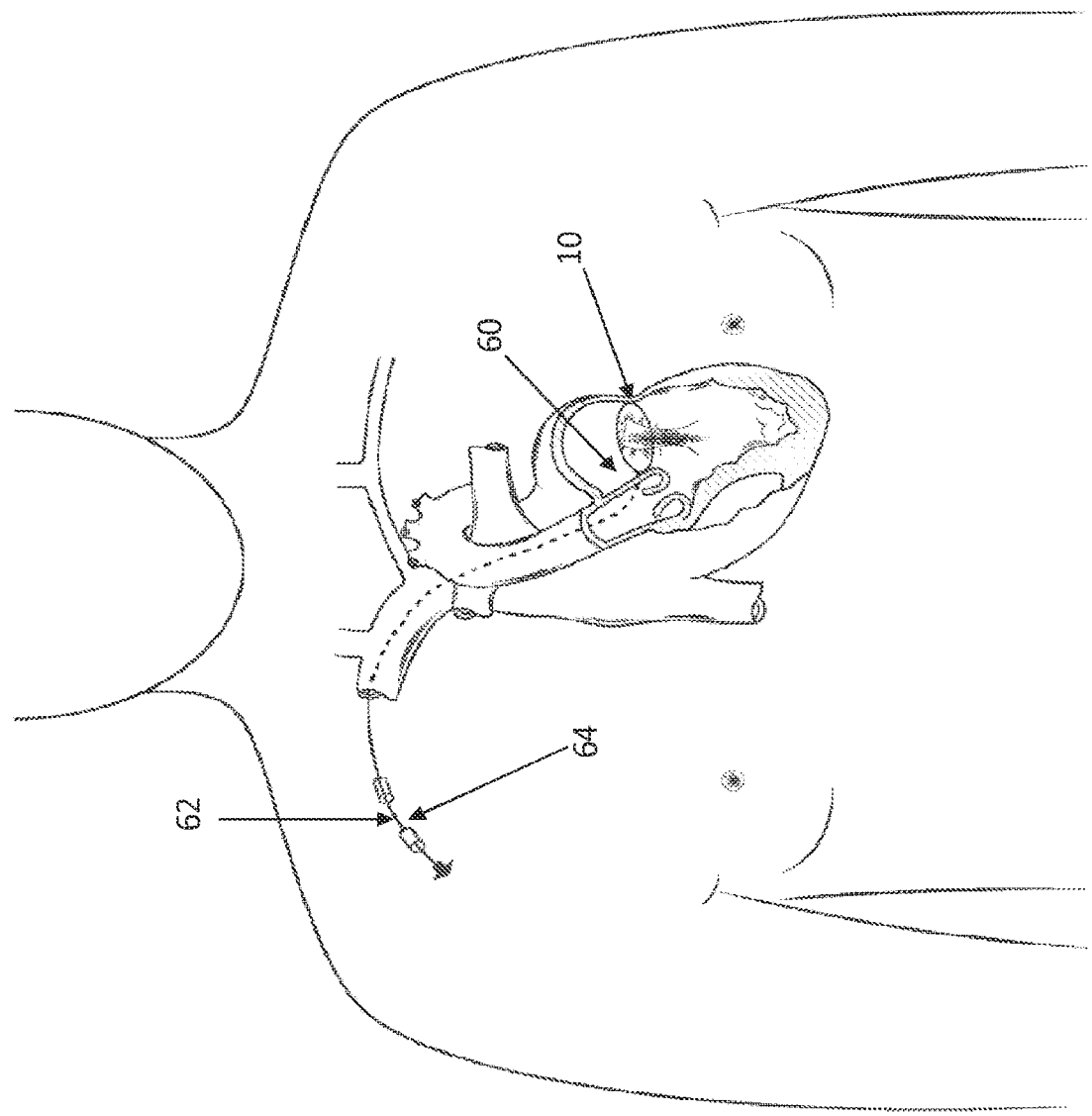
FIG. 42 is a view illustrating manual cinching of the device after tissue healing.

FIG. 42 illustrates manual cinching of the device in a later procedure after tissue healing has occurred as described above with reference to FIG. 14.

Figure 43:
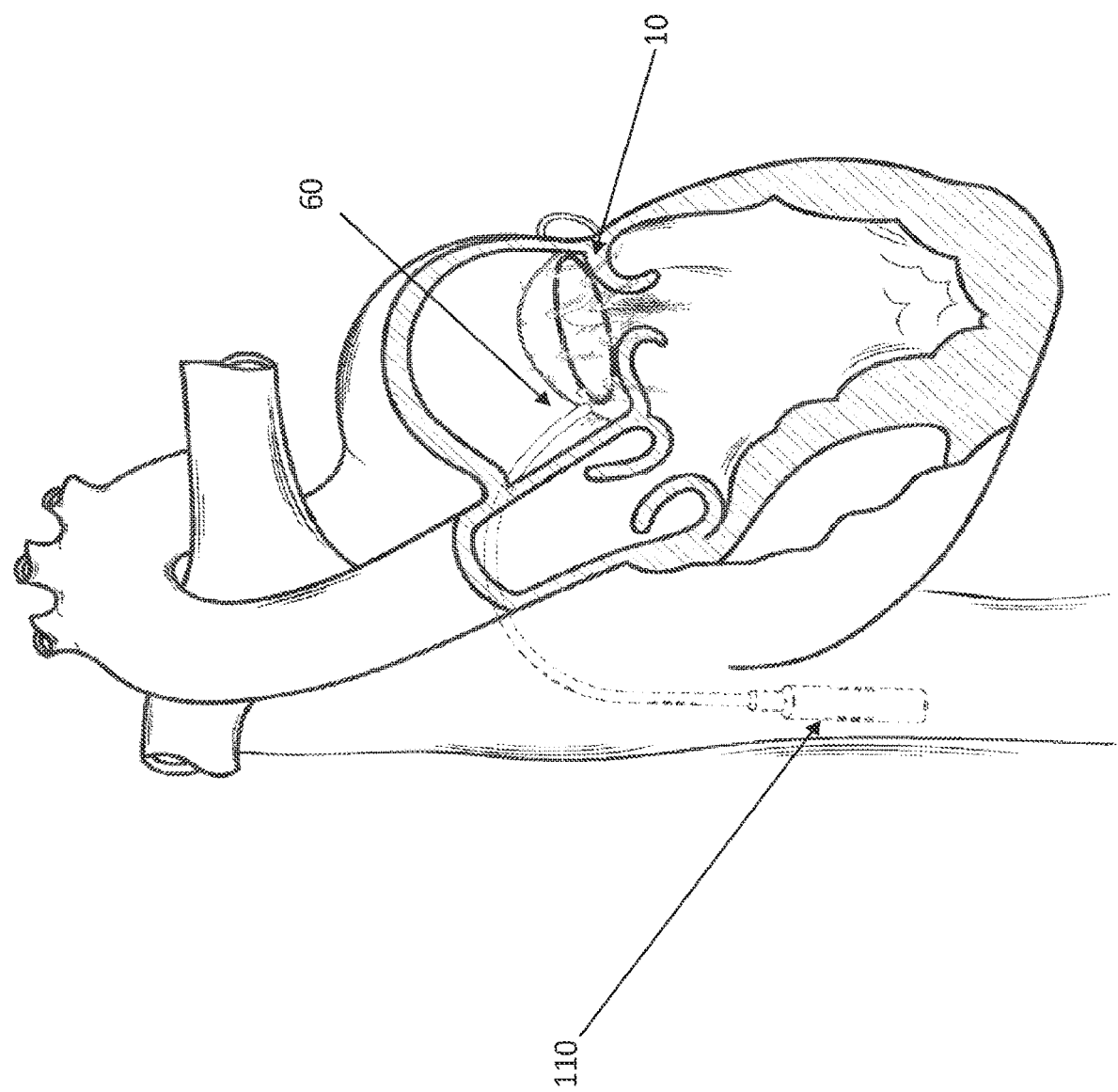
FIG. 43 is a perspective partially cut-away view of the heart illustrating mechanical cinching of the device after tissue healing.

FIG. 43 illustrates cinching of the device in a later procedure after tissue healing has occurred as described above with reference to FIG. 14. Using a mechanical actuator 110 that is implanted during procedure. The mechanical actuator can be actuated and operated magnetically, electrically or by any other appropriate mechanism from outside of the body.

It should be understood that the above description is merely exemplary and that there are various embodiments of the present invention that may be devised, mutatis mutandis, and that the features described in the above-described embodiments, and those not described herein, may be used separately or in any suitable combination; and the invention can be devised in accordance with embodiments not necessarily described above.

What is claimed is:

1. A method for replacing a native valve of a heart located between a ventricle and an atrium, the native valve having leaflets, the leaflets having a ventricle side and an atrium side, the method comprising:
   advancing to the heart an implant comprising (i) a loop of material, and (ii) a plurality of anchors, each of the anchors:
      including a pointed front tip and a linear slot that extends along a longitudinal dimension of the anchor, and
      being coupled to the loop by the loop being threaded through the slot;
   securing the implant to the leaflets of the native valve by penetrating the anchors into the leaflets as the loop slides longitudinally along the slot of each anchor;
   after the implant is attached to the leaflets, advancing a prosthetic valve to the heart; and
   after the prosthetic valve has been advanced through a delivery catheter, expanding the prosthetic valve into the implant so that an interaction between the implant and the prosthetic valve secures the prosthetic valve in place between the ventricle and the atrium.

2. The method of claim 1, wherein after securing the implant and prior to advancing the prosthetic valve, the implant is affixed to the valve leaflets and is retained in place without conforming to a shape of an annulus of the native valve, until such time as the prosthetic valve is deployed into the implant.

3. The method of claim 1, wherein the interaction between the implant and the prosthetic valve comprises friction.

4. The method of claim 1, wherein:
   for each of the anchors, the linear slot extends, along the longitudinal dimension of the anchor, from about halfway along the anchor towards the pointed front tip of the anchor, and
   the plurality of anchors is configured with respect to the loop of material so that contact and sliding motion between the prosthetic valve and the plurality of anchors will reorient the plurality of anchors from an initial orientation to a second orientation at which the anchors are more parallel to each other than in the initial orientation.

5. The method of claim 1, wherein each of the anchors has a a non-slotted rear portion, and wherein the plurality of anchors is configured with respect to the loop of material so that (a) expanding the prosthetic valve within the loop of material will push the rear portions of the plurality of anchors outward, and (b) outward motion of the rear portions of the plurality of anchors will cause the plurality of anchors to pivot so that the pointed front tips of the plurality of anchors move inward, thereby pressing leaflet tissue against the prosthetic valve.

6. The method according to claim 1, wherein penetrating the anchors into the leaflets comprises penetrating the anchors into the leaflets from the ventricle side toward the atrium side.

7. The method according to claim 1, wherein each of the anchors includes a barb that resists withdrawal from the leaflet, and wherein penetrating the anchors into the leaflets comprises penetrating the barbs through the leaflets.

8. The method according to claim 1, wherein the implant includes a plurality of tubes threaded onto the loop.

9. The method according to claim 8, wherein the tubes comprise a material that promotes tissue growth.

10. The method according to claim 1, wherein advancing the implant to the heart comprises advancing the implant to the heart while each of the anchors are associated with a respective launcher, and wherein penetrating the anchors into the leaflets comprises launching the anchors into the leaflets by actuating the launchers.

11. The method according to claim 10, wherein each launcher includes a spring, and wherein, for each of the launchers, actuating the launcher comprises releasing the spring.

12. The method according to claim 10, wherein actuating the launchers comprises actuating the launchers by pulling a pullwire.

13. The method according to claim 1, further comprising, prior to penetrating the anchors into the leaflets, positioning the anchors at the leaflets using a scaffold that includes a plurality of support arms, each of the support arms supporting a respective anchor of the implant.

14. The method according to claim 13, further comprising separating the support arms within the heart by inflating a balloon.

15. The method according to claim 1, wherein the prosthetic valve is self-expanding, and wherein expanding the prosthetic valve comprises releasing the prosthetic valve to self-expand.

16. The method according to claim 1, wherein expanding the prosthetic valve comprises expanding the prosthetic valve by inflating a balloon.

17. The method according to claim 1, wherein advancing the implant to the heart comprises advancing the implant to the heart transapically.

18. The method according to claim 1, wherein advancing the prosthetic valve to the heart comprises advancing the prosthetic valve to the heart during the same procedure as advancing the implant to the heart.

19. The method according to claim 1, wherein advancing the implant to the heart comprises advancing the implant to the heart during a first procedure, and wherein advancing the prosthetic valve to the heart comprises advancing the prosthetic valve to the heart during a second procedure that is separate and subsequent to the first procedure.

* * * * *